United States Patent
Perron et al.

(10) Patent No.: US 9,840,550 B2
(45) Date of Patent: Dec. 12, 2017

(54) COMPOUNDS FOR TREATING THE REMYELINATION BLOCKADE IN DISEASES ASSOCIATED WITH THE EXPRESSION OF HERV-W ENVELOPE PROTEIN

(71) Applicant: GENEURO SA, Plan-les-Ouates (CH)

(72) Inventors: Hervé Perron, Sa

A

B

A

B

A

B

A

B

A

B

A

B

A

B

C

D

A

B

C

D

A

B

C

D

A

B

C

A

B

C

COMPOUNDS FOR TREATING THE REMYELINATION BLOCKADE IN DISEASES ASSOCIATED WITH THE EXPRESSION OF HERV-W ENVELOPE PROTEIN

FIELD OF THE INVENTION

The present application deals with innovative compounds and compositions for preventing and/or treating a newly discovered detrimental mechanism, which blocks the endogenous myelin repair capacity of the adult nervous system (NS) in diseases associated with the expression of HERV-W envelope protein (ENV), in particular of its MSRV subtype.

This novel therapeutic approach combines an inhibition of the upstream pathogenic effects of Env on oligodendrocyte precursor cells (OPCs) together with an inhibition of the final downstream effectors of the Env pathogenicity on OPC differentiation (NO radicals), which are now shown to block remyelination of HERV-W associated diseases affecting the nervous system.

The present invention deals with therapeutic compositions comprising (i) at least one an anti-HERV-W Env ligand and/or (ii) at least one Nitric Oxyde free radical (NO) inhibitory drug for its use for the prevention and/or the treatment of the remyelination blockage in diseases associated with the expression of HERV-W envelope protein (ENV), in particular of its MSRV subtype.

The composition when combining both ligand and NO inhibitory drug(s) targets the upstream Env inducer as well as the downstream NO effectors in this newly deciphered process causing re-myelination blockade in NS lesions.

Moreover, synergistic action of the two types of compounds (targeting Env and NO, respectively) enhances the rapidity and the efficacy of a therapy in patients with non-remyelinating lesions induced by the activation of HERV-W (in particular when associated with MSRV subtype, isolated as virion particles from MS cells[1]) and by the expression of its Env protein in the nervous system.

DETAILED DESCRIPTION OF THE INVENTION

Figure 1:
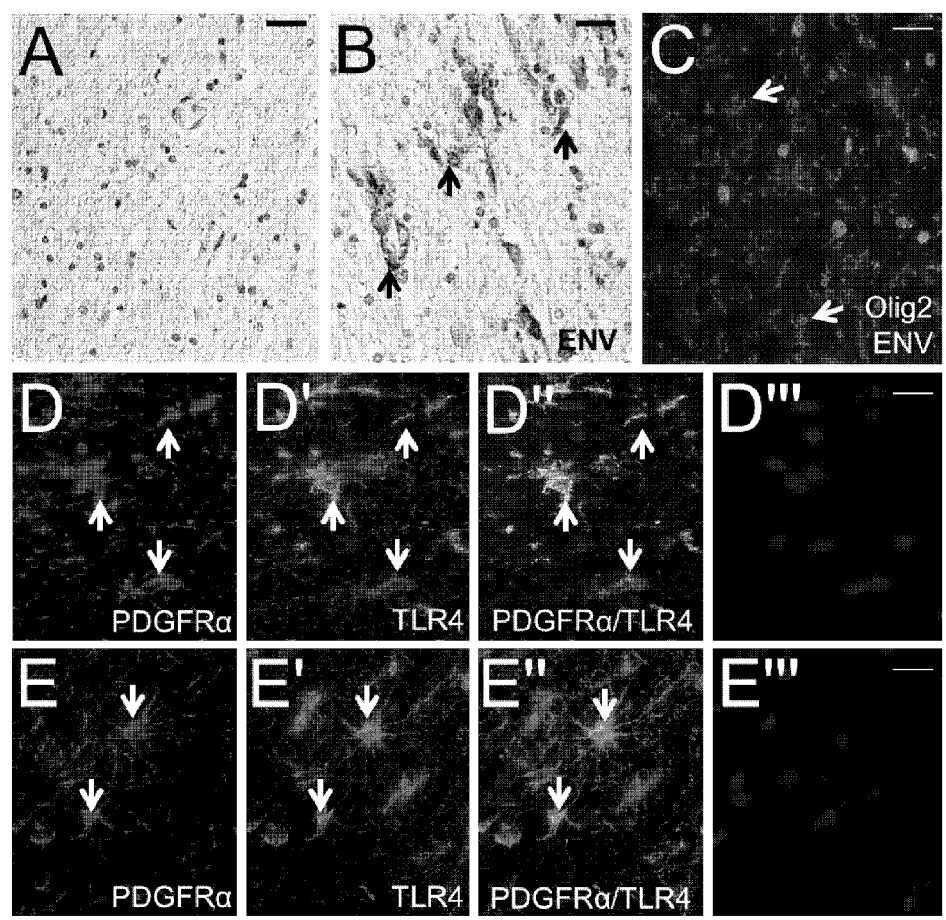

According to a first aspect, the present invention deals with an anti-HERV-W Env ligand for its use for the prevention and/or the treatment of the remyelination blockage in diseases associated with the expression of HERV-W envelope protein (ENV), in particular of its MSRV subtype In the present invention, the terms "differentiation blockade", "remyelination blockade" or "remyelination blockage" are used to summarize the newly discovered phenomenon consisting in (i) the inhibition of Oligodendrocyte Precursor Cells (OPCs) differentiation induced by HERV-W envelope protein (in particular from MSRV subtype), (ii) the resulting production of NO from OPCs and (iii) the resulting inhibition of Myelin production by OPCs, as described in Example 1.

The diseases associated with the expression of HERV-W envelope protein (ENV), in particular of its MSRV subtype are defined as HERV-W associated diseases affecting the nervous system and more particularly, but in a non limitative manner: Multiple Sclerosis (MS), more particularly of Remitting-Relapsing Multiple Sclerosis (RRMS), the progressive Multiple Sclerosis such as Secondary Progressive Multiple Sclerosis (SPMS) or Primary Progressive Multiple Sclerosis (PPMS), Chronic Inflammatory Demyelinating Polyneuropathy (CIDP[2]), psychoses such as Schizophrenia and bipolar Disorder[6], in which myelin impairment is also described[3-5].

Classically, multiple-sclerosis (MS) lesions are attributed to an immune-mediated loss of oligodendrocytes and of myelin sheaths with axonal damage. The effects on immune cells that are mediated by the Multiple Sclerosis associated retrovirus (MSRV) envelope protein (Env) from the HERV-W family of endogenous retroviruses in association with nervous system (NS) inflammatory lesions have been described[7]. However, a direct pathogenicity of MSRV-Env on glial cells involving the blockade of MS plaques remyelination by Oligodendrocyte precursor cells (OPC) was previously unknown and had never been shown.

According to one aspect of the present invention, the inhibition of the upstream pathogenic effects of Env on oligodendrocyte precursor cells (OPCs) is done using an anti-HERV-W Env ligand. The anti-HERV-W Env ligand of the present invention is defined by its ability to bind to the Env protein.

The term "bind" or "binding" of the ligand means an at least temporary interaction or association with or to a target antigen, e.g. ENV, comprising fragments thereof containing an epitope.

According to the present invention, HERV-W ENV means protein encoded by the env gene of any member of the HERV-W family, including the MSRV subgroup as defined from sequences identified in RNA of retroviral particles from MS[14, 23].

The ligand of the present invention can also be defined as being comprised within a recombinant scFV protein, a Fab fragment, an antibody, said antibody can be a polyclonal, monoclonal, oligoclonal, a chimerized, engineered or a humanized or a human antibody. In a particular aspect of the invention, the antibody comprising the ligand is a humanized or a human IgG, and more particularly an IgG1 or an IgG4.

More particularly, the ligand of the present invention comprises at least one and more preferably each of the complementary-determining regions (CDRs) having the amino acid sequences SEQ ID No. 1, SEQ ID No. 2, SEQ ID No. 3, SEQ ID No. 4, SEQ ID No. 5 and SEQ ID No. 6.

The above mentioned ligand comprises at least one and more preferably each of the complementary-determining regions (CDRs) encoded by SEQ ID No. 25, SEQ ID No. 26, SEQ ID No. 27, SEQ ID No. 28, SEQ ID No. 29, SEQ ID No. 30.

As stated above, the remyelination blockade also results in production of NO from OPCs. Then according to a further aspect, the present invention also deals with a Nitric Oxyde radical inhibitory drug for its use for the prevention and/or the treatment of the remyelination blockage in diseases associated with the expression of HERV-W envelope protein (ENV), in particular of its MSRV subtype.

The diseases associated with the expression of HERVW ENV are those defined above.

In a more specific aspect of the invention a Nitric Oxyde free radical (NO) inhibitory drug, Nitric Oxyde radical inhibitory drug or NO inhibitory drug is any drug that can inhibit the biological effects of NO molecules, also named NO radicals. NO inhibitory drugs are chosen among $N^g$-nitro-L-arginine-methylester (L-NAME), S-methyl-isothiourea (SMT), fumaric acid or dimethyl fumarate (DMF).

In another aspect, the present invention deals with a pharmaceutical composition combining at least an anti-MSRV/HERV-W Env ligand as defined above and at least one Nitric Oxyde radical inhibitory drug as defined above.

This composition being used in for the prevention and/or the treatment of the remyelination blockage in diseases associated with the expression of HERV-W envelope protein (ENV), in particular of its MSRV subtype, the diseases being those defined above.

The pharmaceutical product containing an anti-HERV-W Env ligand as defined above; and a Nitric Oxyde radical inhibitory drug as defined above are considered as a combination product for simultaneous, separate or spread over time administration for preventing and/or treating the remyelination blockage in diseases associated with the expression of HERV-W envelope protein (ENV), in particular of its MSRV subtype.

According to the results described below on mouse models of experimental allergic encephalomyelitis (EAE) induced by Env, a synergistic effect of the combination an anti-MSRV/HERV-W Env ligand with at least one of these NO-inhibiting molecules was shown, compared to any of these therapeutic agents given alone. Even when given alone, Nitric Oxyde radical inhibitory drug or the anti-MSRV/HERV-W Env ligand show therapeutic efficacy with recovery of clinical deficit known to be associated with myelin lesions in EAE[8]. Nonetheless, the comparison between (i) Nitric Oxyde radical inhibitory drug or the anti-MSRV/HERV-W Env ligand and (ii) combination of at least one Nitric Oxyde radical inhibitory drug and at least one anti-MSRV/HERV-W Env ligand evidences a great advantage of using this combination in the course of the treatment.

Thus, the absence of inflammatory infiltrates and/or lesions with inflammatory activity (e.g. inactive plaques of MS) does not preclude treating the remyelination blockade induced by Env in affected patients. This is of particular relevance in patients with progressive MS (primary or secondary progressive forms) known to have numerous lesions without inflammatory activity, which no longer show gadolinium enhancement of magnetic resonance imaging signal in most brain and spinal cord lesions.

The present invention also deals with a method for preventing and/or treating of the remyelination blockage in diseases associated with the expression of HERV-W envelope protein (ENV), in particular of its MSRV subtype comprising the administration of at least one anti-MSRV/HERV-W Env ligand to a human being.

In a specific aspect, the method further comprises the administration of at least one Nitric Oxyde radical inhibitory drug.

In another aspect, the invention deals with a method for preventing and/or treating of the remyelination blockage in diseases associated with the expression of HERV-W envelope protein (ENV), in particular of its MSRV subtype comprising the administration of at least one Nitric Oxyde radical inhibitory drug to a human being.

DESCRIPTION OF THE FIGURES

FIG. 1. Detection of Env protein and TLR4 receptor expression in MS tissue. (A,B) Anti-Env immunohistochemistry revealed Env protein (arrows) in NAWM close to a chronic active lesion (B) but not in healthy brain white matter (A). (C) Olig2-positive OPCs in close vicinity to Env-positive microglial cells at the rim of a chronic active lesion. (D-D''') Healthy control brain tissue with PDGFRα-positive OPCs featuring co-expression of TLR4 (arrows). (E-E''') OPCs in NAWM close to an active lesion of an MS patient expressing both TLR4 and PDGFRα (arrows). Scale bars: 50 μm.

FIG. 2. Regulation of TLR4 expression during OPC differentiation. (A) Quantitative RT-PCR showing a progressive down regulation of TLR4 expression during spontaneous rat OPC differentiation in culture over a period of nine days. GAPDH expression was used as reference gene. Data are shown as mean values+/−standard deviation derived from 3 independent experiments. t-test (***$P<0.001$). (B,B') Anti-TLR4 immuno-staining demonstrated that upon small-hairpin RNA (shRNA)-mediated suppression of TLR4, transfected OPCs were devoid of TLR4 expression (arrow) ensuring antibody specificity. OPCs shown were fixed three days post transfection and transfected cells were marked by expression of eGFP. Note that the neighboring untransfected cells were TLR4 positive. (C-D') Representative examples of galactocerebroside (GalC)/TLR4 double-positive OPCs after three days (C,C') and myelin basic protein (MBP)/TLR4 double-positive OPCs after six days (D,D') of spontaneous differentiation in culture. Arrowheads in (D) point to more highly differentiated OPCs featuring only reduced levels of TLR4 expression thus reflecting gene expression data shown in (A). Arrows indicate strongly expressing less mature cells.

FIG. 3. Proinflammatory effects of recombinant Env on cultured rat OPCs. (A, B, C) Stimulation of OPCs by recombinant Env in solution (A, Env soluble), surface-bound recombinant Env (B; Env solid) and membrane-bound Env (C) expressed on pV14Env-transfected U343 glioblastoma cells (D-D') all lead to a strong induction of iNOS expression after eight hours of stimulation as compared to respective buffer controls or to OPCs grown in presence of pV14ctrl-transfected U343 glioblastoma cells (E-E'). In the recombinant Env preparation endotoxin levels were <5 EU/mL as measured by LAL test. (D-E') anti-Env immuno-stainings of pV14Env and pV14ctrl transfected U343 cells revealing Env surface expression. (F-G') Oligodendroglial morphology as evaluated by O4 immuno-stainings remains unaltered upon stimulation with surface-bound recombinant Env shown after one day (F,F') as well as after five days (G,G') in culture. (H) Indirect spectrometric analysis of cell culture supernatants measuring the NO disintegration product nitrite revealed significantly increased dose-dependent levels of NO in OPC samples stimulated by soluble recombinant Env for 24 h. (I-K) Proinflammatory cytokines such as TNFα, IL-1β and IL-6 undergo up regulation upon stimulation with surface-bound recombinant Env. GAPDH was used as reference gene. Data are shown as mean values+/−standard deviation and represent 1 out of 6 (A), 8 (B), 3 (C), 3 (H) and 8 (I-K) independent experiments, respectively. t-test (***$P<0.001$). Scale bars: 50 μm.

FIG. 4. Comparison of sensitivity to HERV-W Env in immature (one day-old=OPC) and matured rat OPCs (seven days old; "matured OPCs" or Oligodendrocytes=OL). Both cell types were subjected to stimulation with 100 ng/ml soluble recombinant Env. Although significant in comparison to buffer controls iNOS and cytokine up regulation upon Env stimulation in OLs is less pronounced as compared to OPCs. GAPDH expression was used as reference gene. Data are shown as mean values+/−standard deviation and derive from one representative out of 3 independent experiments. t-test (*$P<0.001$; $P<0.01$; *$P<0.05$).

FIG. 5. Env dependent reactions of human OPCs. (A) Stimulation of cultured human OPCs with surface-bound (solid) and soluble recombinant (soluble) Env lead to a strong induction of iNOS expression in after 24 h of stimulation as compared to buffer treated cells. GAPDH expression was used as reference gene. Data are shown as mean values+/−standard deviation and derive from one representative out of 3 independent experiments. t-test (***P<0.001). (B,B') Immunofluorescent stainings of cultured GalC positive human OPCs reveal a strong signal for TLR4 (shown after three days in culture). Scale bars: 50 µm.

Figure 6:
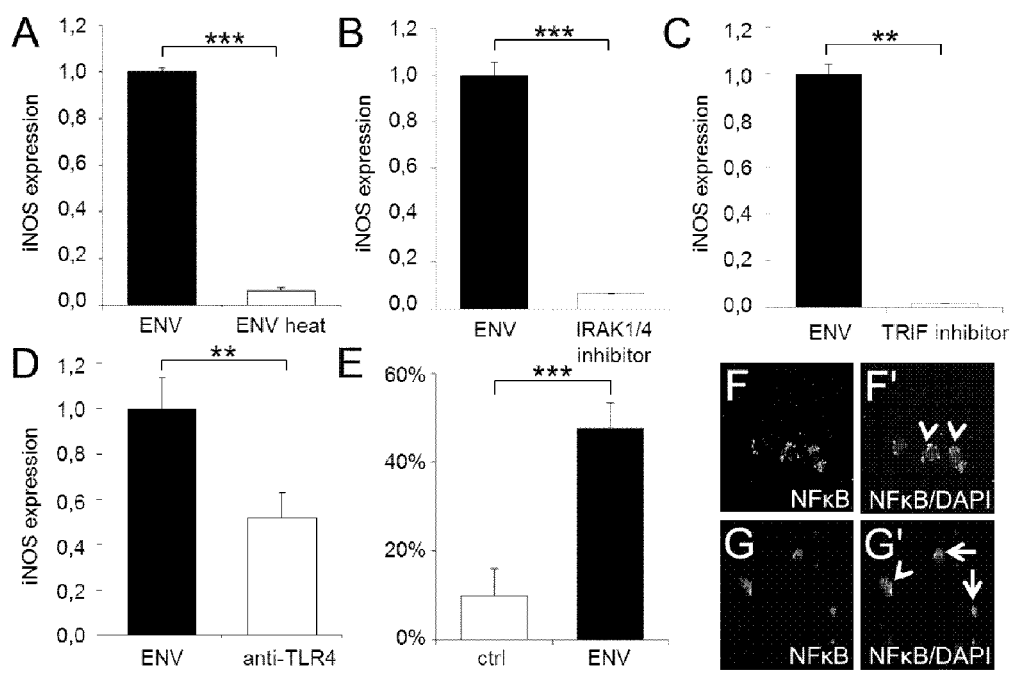

FIG. 6. Env pathway neutralization experiments. (A) Heat inactivation of recombinant Env lead to an abrogated iNOS gene induction as compared to native recombinant Env after 8 h of OPC stimulation. Both preparations, native Env and denatured Env (Env heat) were applied at a concentration of 1000 ng/ml. (B,C) Reduction of iNOS expression in OPCs upon pharmacological inhibition of IRAK1/4 and TRIF, respectively. Following a 2 h pre-incubation step with 3200 nM IRAK1/4 inhibitor I or 50 µm TRIF inhibitory peptide OPCs were stimulated with surface-bound (solid) recombinant Env for 8 h and subsequently lysed. (D) Reduction of iNOS expression in OPCs following antibody-mediated blockade of Env receptor TLR4. Following a 2 h pre-incubation step with anti-TLR4 antibody at a concentration of 15 µg/ml at 37° C., OPCs were stimulated with solid rEnv for 8 h and then lysed. GAPDH expression was used as reference gene. Data are shown as mean values+/−standard deviation and derive from one representative out of 3 independent experiments each. t-test (*P<0.001, P<0.01). (E) Increased nuclear localisation of NFκB following stimulation of OPCs with surface-bound (solid) recombinant Env for 8 h. Data are shown as mean values+/−standard deviation and derive from one representative out of 3 independent experiments each. t-test (***P<0.001). (F-G') Representative NFκB immunostainings of buffer (control) and Env stimulated OPCs. Scale bars: 50 µm.

Figure 7:
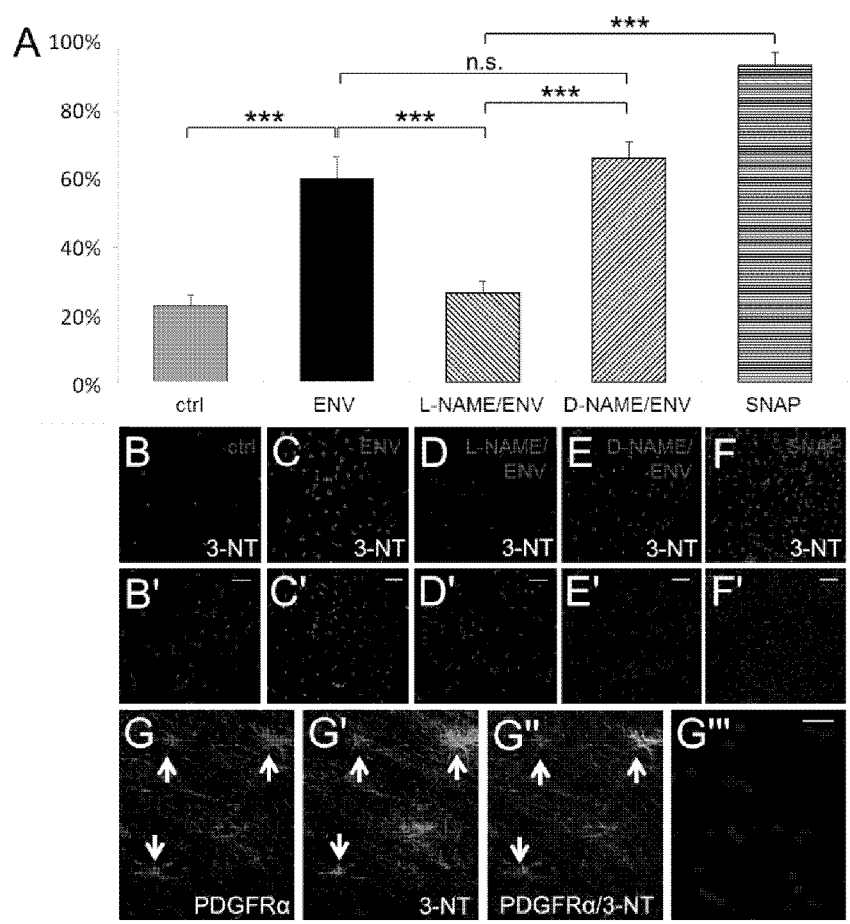

FIG. 7. Generation of 3-nitrotyrosine (3-NT) positive OPCs. (A) Immunofluorescent stainings revealed that following 24 h of Env stimulation (surface bound recombinant Env) significantly more OPCs expressed the NO-dependent nitrosative stress marker 3-NT as compared to buffer treated cells. As positive control S-nitroso-N-acetylpenicillamine (SNAP), a strong NO donor, was used. However, when OPCs were incubated with L-NAME, an iNOS inhibitory molecule, at a concentration of 100 µM for 30 min at 37° C. prior to Env stimulation, 3-NT positivity was reduced to control levels. The inactive enantiomer D-NAME could not abolish the Env dependent 3-NT induction. Data are shown as mean values+/−standard deviation and derive from one representative out of 3 independent experiments. t-test (***P<0.001). (B-F') Representative anti-3-NT immunostainings of control cells (B,B'), Env stimulated OPCs (C,C'), OPCs preincubated with L-NAME (D,D'), D-NAME (E,E') and OPCs exposed to SNAP (F,F'). Scale bars: 50 µm. (G-G''') Immunohistofluorescent stainings of MS patient NAWM tissue sections demonstrated that resident OPCs (marked by their expression of the precursor marker PDGFRα, arrows) can undergo nitrosative stress as revealed by their 3-NT positivity.

Figure 8:
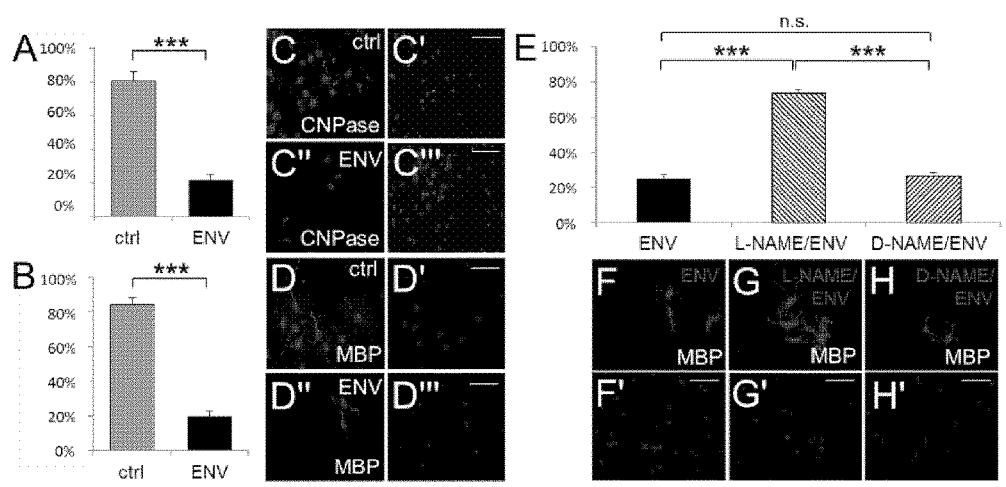

FIG. 8. Env dependent inhibition of OPC differentiation. (A,B) Immunofluorecent analysis demonstrating that following one day and three days of stimulation with surface bound recombinant Env, a significantly decreased number of OPCs expressed the early myelin marker CNPase as well as the late myelin marker MBPas compared to control cells. Data are shown as mean values+/−standard deviation and derive from one representative out of 4 independent experiments. t-test (*P<0.001). (C-C''') and (D-D''') show representative anti-CNPase and anti-MBP immunostainings of control and Env-stimulated OPCs. (E) Incubation of OPCs with 100 µm L-NAME in combination with surface bound recombinant Env for three days lead to the abolishment of the Env-mediated OPC differentiation block as revealed by anti-MBP immunostaings. Application of D-NAME was not able to rescue myelin expression. Data are shown as mean values+/−standard deviation and derive from one representative out of 4 independent experiments. t-test (*P<0.001; n.s. not significant). (F-H') Representative MBP immunostainings of OPCs stimulated with Env alone, a combination of Env and L-NAME and a combination of Env and D-NAME, respectively. Scale bars: 50 µm.

Figure 9:
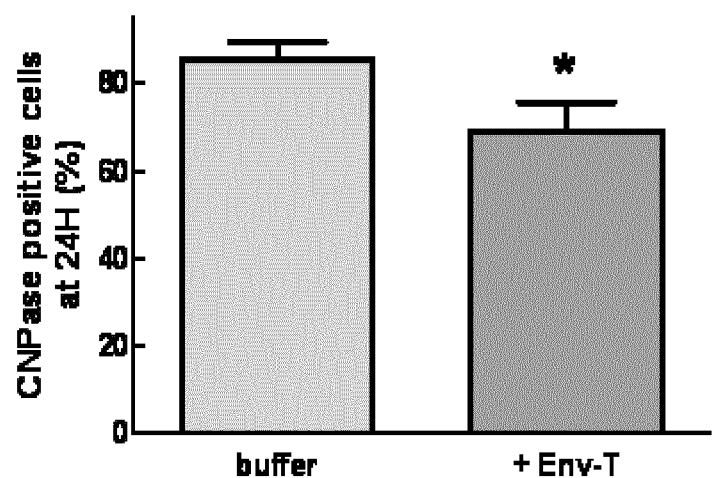
Figure 9:
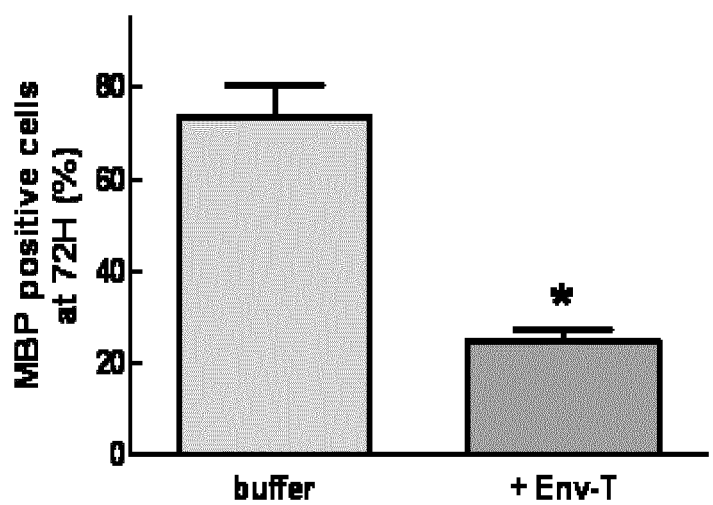

FIG. 9. Expression of OPC maturation markers after 24 and 72 hours of stimulation in labteks pre-coated with MSRV-Env. Coated MSRV-Env (+Env-T) induced a decrease in the percentage of CNPase positive OPC after 24 hours of stimulation (A), as well as a decrease in the percentage of MBP positive OPC after 72 hours of stimulation (B), when compared to its dilution buffer (buffer). Data are presented as Mean±SEM of one experiment assessed in decaplicates (410 to 563 counted cells per group; *p<0.05 t-test (A) and 364 to 491 counted cells per group; *p<0.001 Mann-Whitney Rank Sum test (B)).

Figure 10:
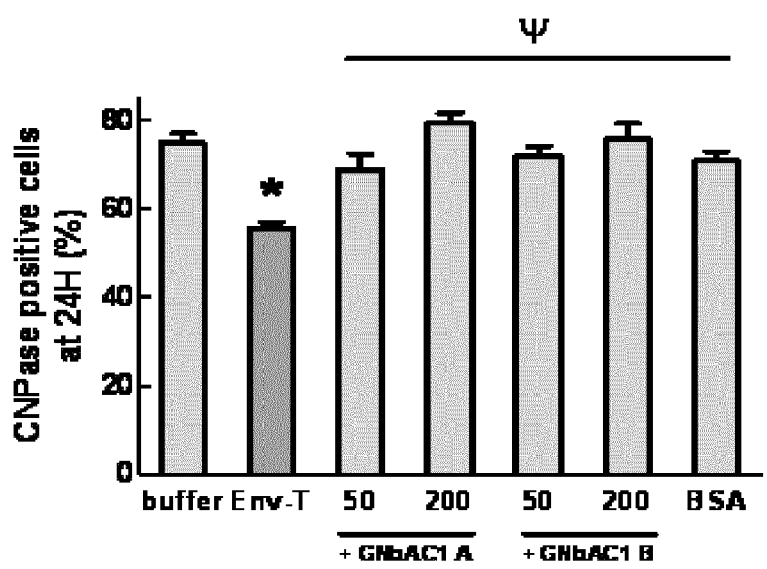
Figure 10:
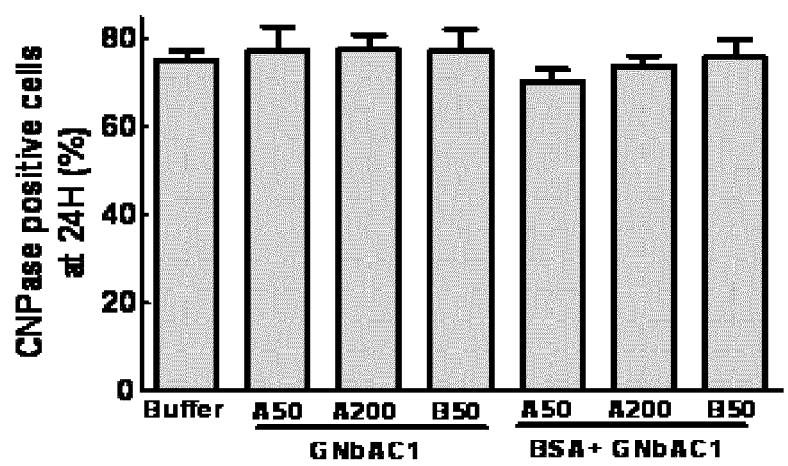

FIG. 10. Expression of CNPase in human OPC after 24 hours of stimulation by MSRV-Env and GNbAC1. (A) Coated MSRV-Env induces a decrease in the percentage of CNPase positive OPC after 24 hours of stimulation. GNbAC1 at 50 nM or 200 nM fully inhibits MSRV-Env effect, in both GNbAC1 treatments protocols tested (GN-bAC1-A or GNbAC1-B). Data are presented as Mean±SEM of 2 to 8 independent experiments (705 to 3878 counted cells per group). (B) GNbAC1 (50 nM or 200 nM) coated alone or together with BSA (1 µg/ml), in both GNbAC1 treatments protocols tested (GNbAC1-A or GNbAC1-B) has no effect on the percentage of CNPase positive OPC. Data are presented as Mean±SEM of one experiment assessed in decaplicates (399 to 512 counted cells per group; p>0.05; One-way ANOVA).

Figure 11:
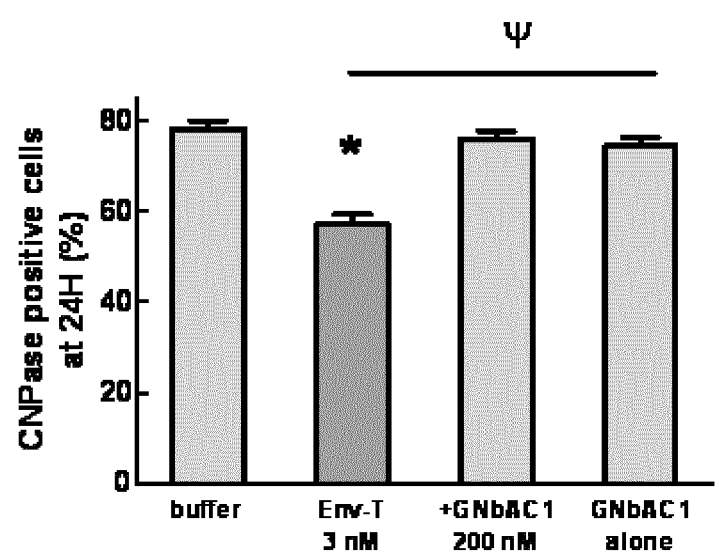

FIG. 11. Expression of CNPase in human OPC cultures after 24 hours of stimulation by MSRV-Env and GNbAC1 added to the culture medium. MSRV-Env (3 nM) diluted in the cell culture medium significantly decreases the CNPase expression after 24 hours of treatment. GNbAC1 (200 nM) inhibits completely this effect, while it does not show any effect alone. Data are presented as Mean±SEM of 2 to 4 independent experiments (927 to 1913 counted cells per group); *p<0.001 vs Buffer; One-way ANOVA followed by Fischer LSD post-hoc analyses).

Figure 12:
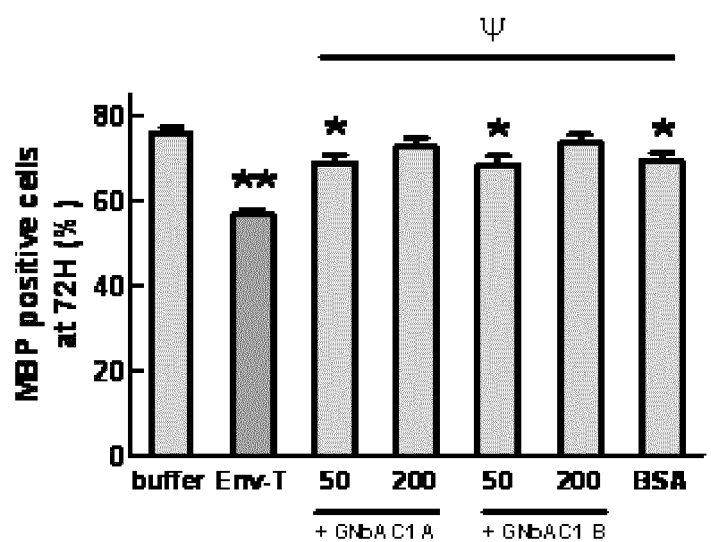
Figure 12:
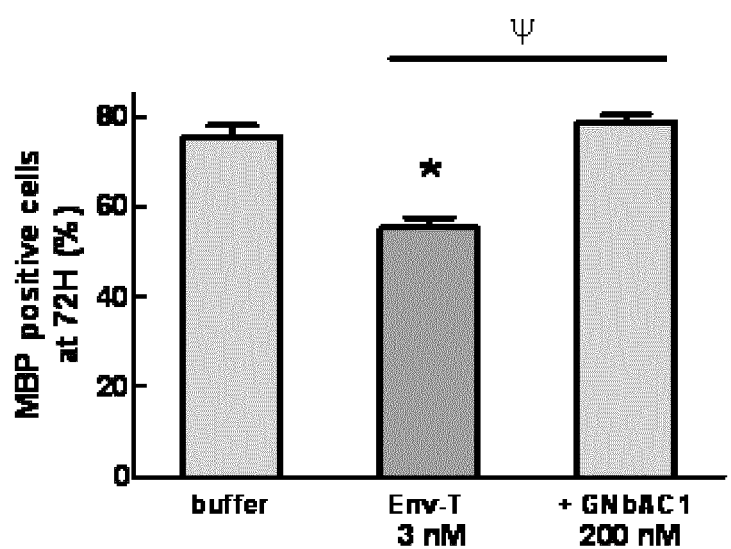

FIG. 12. Expression of MBP in human OPC cultures after 72 hours of stimulation by MSRV-Env and GNbAC1. (A) Coated MSRV-Env (Env-T) induces a decrease in the percentage of MBP positive OPC after 72 hours of stimulation. GNbAC1 at 50 nM partially inhibits MSRV-Env effect, and this inhibition is complete at 200 nM, in both GNbAC1 treatments protocols tested (GNbAC1-A or GNbAC1-B). (B) MSRV-Env (3 nM) added in the cell culture medium significantly decreases MBP expression after 72 hours of treatment. GNbAC1 (200 nM) inhibits completely this effect (B).

Data are presented as Mean±SEM of (A) 2 to 8 independent experiments (924 to 4156 counted cells per group) *p<0.05; **p<0.001 vs buffer; ψp<0.001 vs Env-T; One-way ANOVA followed by Fisher LSD post-hoc analysis, and of (B) 2 to 4 independent experiments (1013 to 1834 counted cells per group; *p<0.001 vs buffer; ψp<0.001 vs Env-T; One-way ANOVA followed by Fisher LSD post-hoc analysis).

Figure 13:
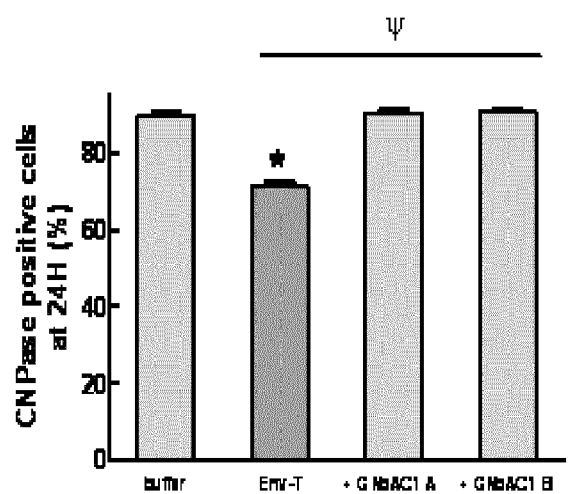
Figure 13:
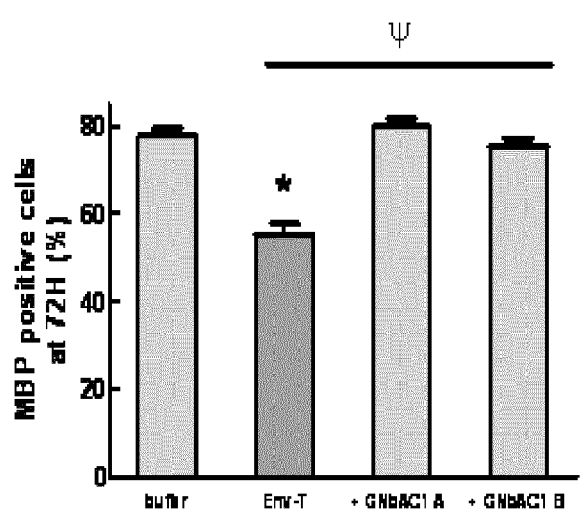

FIG. 13. Expression of OPC maturation markers after 24 and 72 hours of stimulation by coated MSRV-Env and GNbAC1. Coated MSRV-Env induces (A) a decrease in the percentage of CNPase positive human OPC after 24 hours of stimulation as well as (B) a decrease in the percentage of MBP positive human OPC after 72 hours of stimulation. (A) GNbAC1 (200 nM) fully inhibits MSRV-Env effect, in both GNbAC1 treatments protocols tested (GNbAC1-A or GNbAC1-B). Data are presented as Mean±SEM of 6 independent experiments (2805 to 3039 counted cells per group; *p<0.05 vs buffer; ψp<0.05 vs MSRV-Env; Kruskal-Wallis ANOVA-1 on Ranks followed by Student Newman Keuls post-hoc analysis and (B) 5 to 6 independent experiments (1671 to 2066 counted cells per group; *p<0.05 vs buffer; ψp<0.05 vs MSRV-Env; Kruskal-Wallis ANOVA-1 on Ranks followed by Dunn post-hoc analysis).

Figure 14:
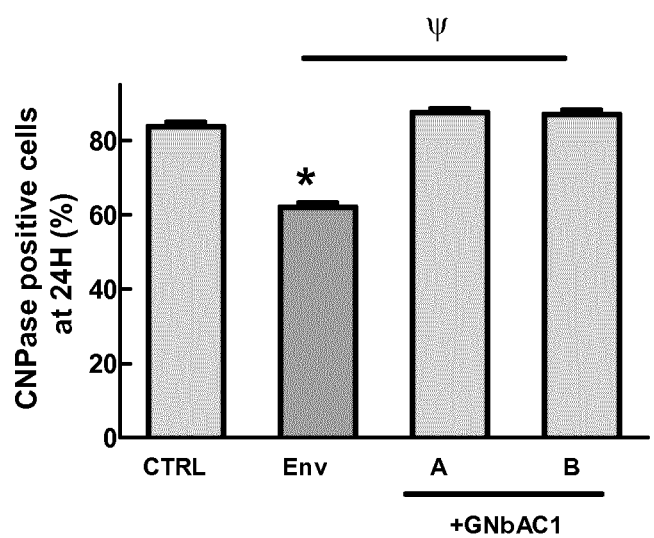
Figure 14:
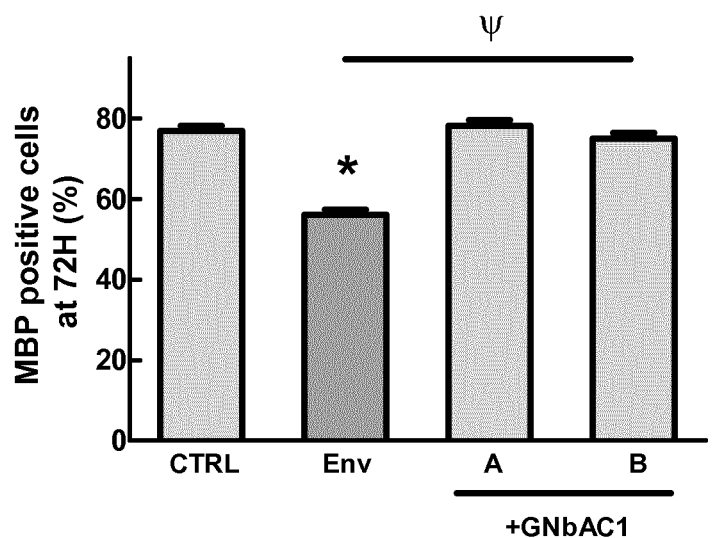

FIG. 14. Inhibition of human OPC maturation induced by MSRV-Env is completely reversed by GNbAC1. Coated MSRV-Env (Env) induces (A) a decrease in the percentage of CNPase positive human OPC after 24 hours of stimulation as well as (B) a decrease in the percentage of MBP positive human OPC after 72 hours of stimulatio. GNbAC1 (200 nM) fully inhibits MSRV-Env effect, in both GNbAC1 treatments protocols tested (+GNbAC1 A or +GNbAC1 B). Results are expressed as the percentage of CNPase (A) or MBP (B) positive cells and represent the Mean±SEM of 8-14 independent experiments (3600 to 6800 counted cells per group (A) and 2700 to 5800 counted cells per group (B)). *p<0.05 Vs CTRL; ψp<0.05 Vs MSRV-Env; Kruskal-Wallis ANOVA-1 on Ranks followed by Dunn post-hoc analysis.

Figure 15:
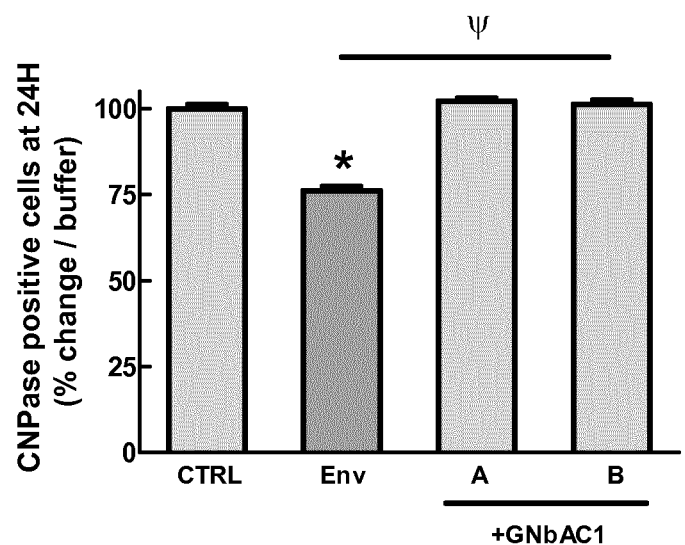
Figure 15:
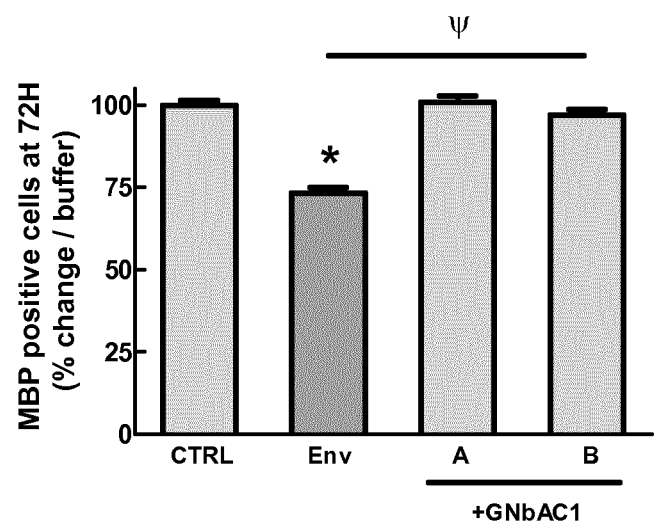

FIG. 15. Inhibition of human OPC maturation induced by MSRV-Env is completely reversed by GNbAC1 (normalized data). MSRV-Env was coated on culture chambers slides before seeding OPCs. GNbAC1 (200 nM) is mixed with MSRV-Env before coating (GNbAC1-A) or incubated on culture chambers coated with MSRV-Env (GNbAC1-B). Data are quantified as the percentage of (A) CNPase or (B) MBP positive cells and are expressed as the percentage of change to the CTRL condition (MSRV-Env Buffer). Results represent the Mean±SEM of 8-14 independent experiments (3600 to 6800 counted cells per group (A) and 2700 to 5800 counted cells per group (B)). *p<0.05 Vs CTRL; ψp<0.05 Vs MSRV-Env; Kruskal-Wallis ANOVA-1 on Ranks followed by Dunn post-hoc analysis.

Figure 16:
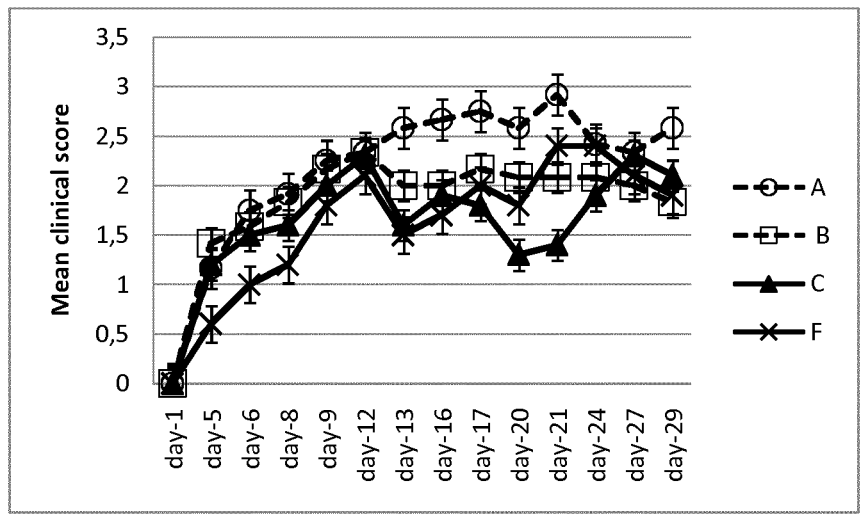

FIG. 16. EAE clinical score kinetics of Groups A, B, C and F (A—Untreated EAE positive controls, B—EAE treated with GNbAc1 200 μg, C—EAE treated with L-NAME, F—EAE treated with GNbAc 200 μg+L-NAME).

Figure 17:
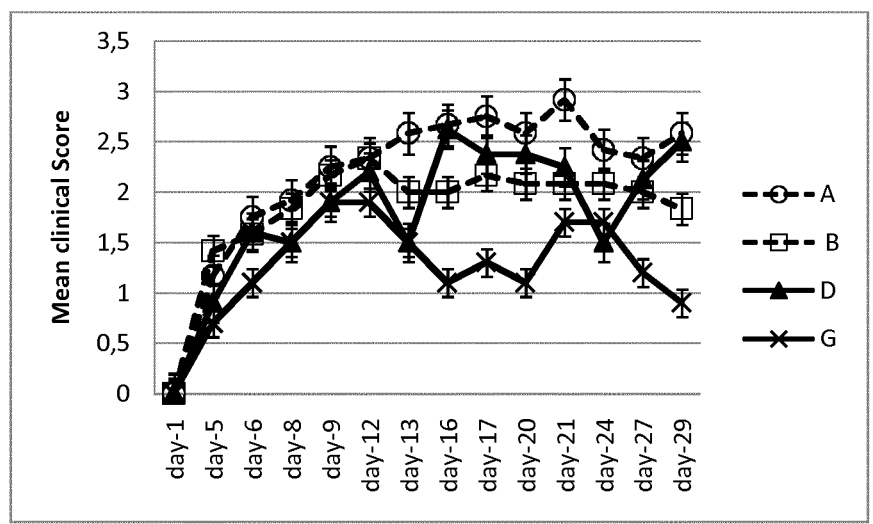

FIG. 17. EAE clinical score kinetics of Groups A, B, D and G (A—Untreated EAE positive controls, B—EAE treated with GNbAc1 200 μg, D—EAE treated with SMT, G—EAE treated with GNbAc 200 μg+SMT)

Figure 18:
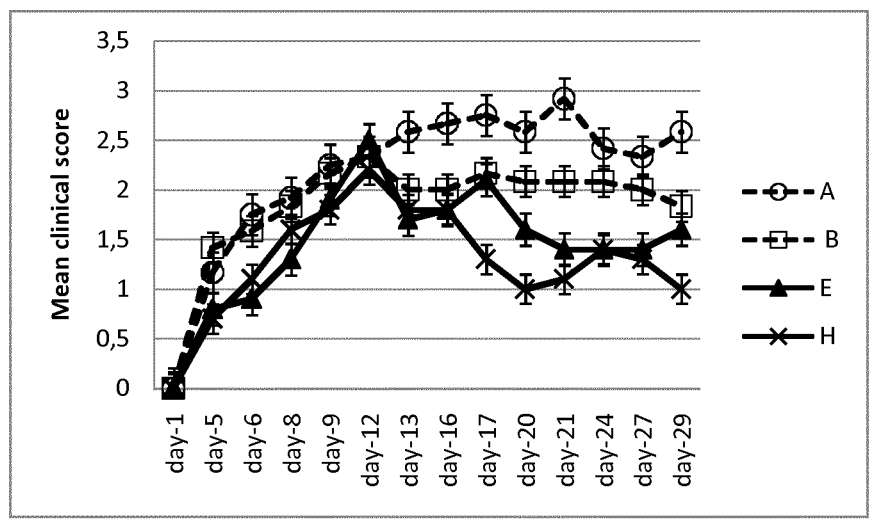

FIG. 18. EAE clinical score kinetics of Groups A, B, E and H (A—Untreated EAE positive controls, B—EAE treated with GNbAc1 200 μg, E—EAE treated with DMF, H—EAE treated with GNbAc 200 μg+DMF)

Figure 19:
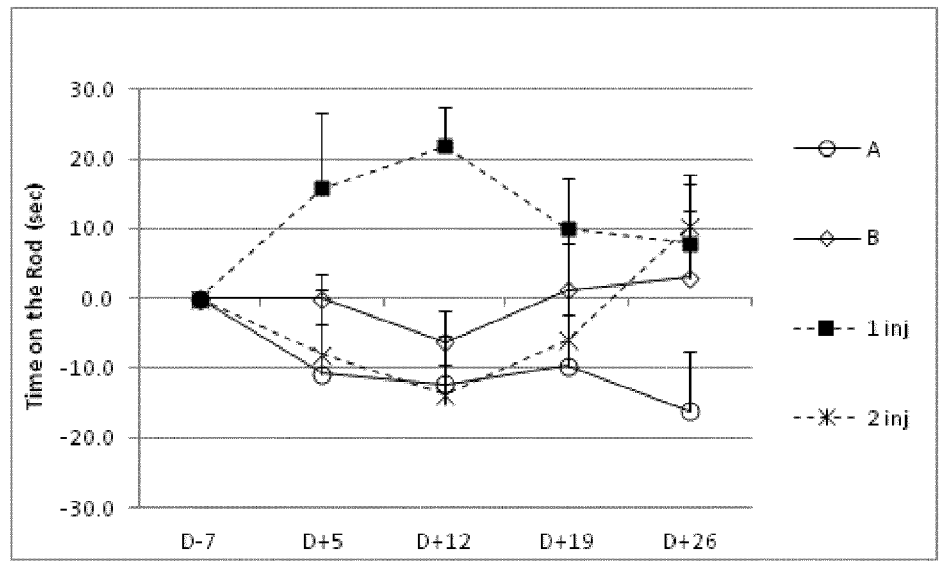
Figure 19:
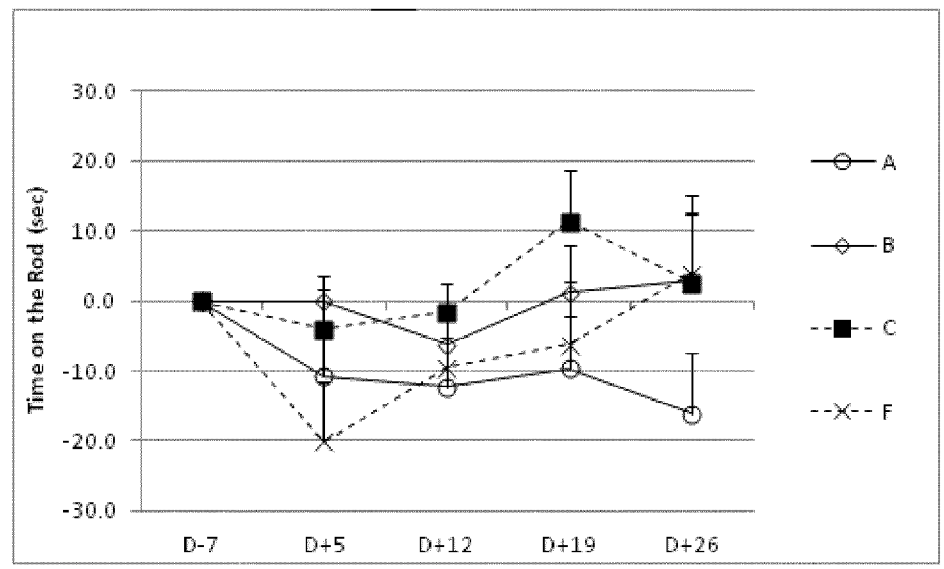
Figure 19:
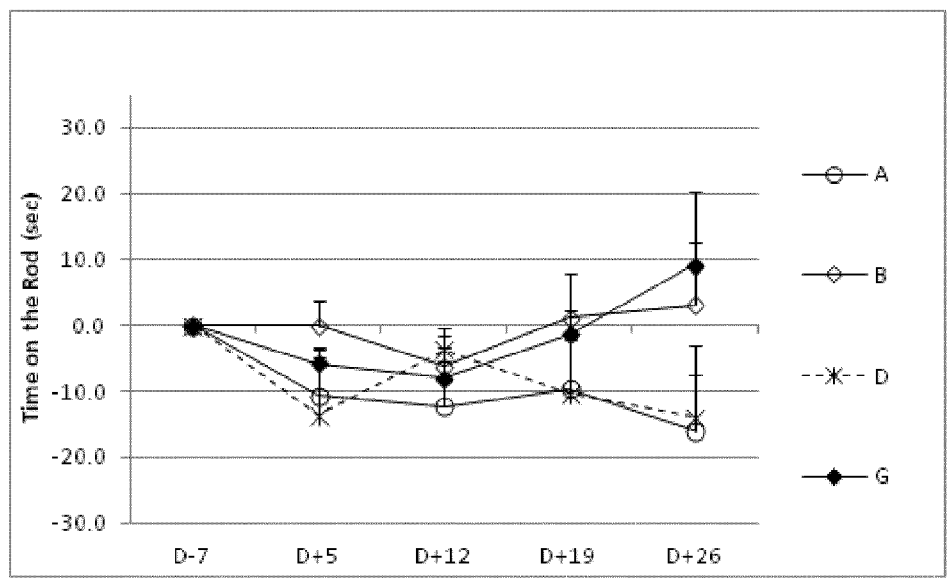
Figure 19:
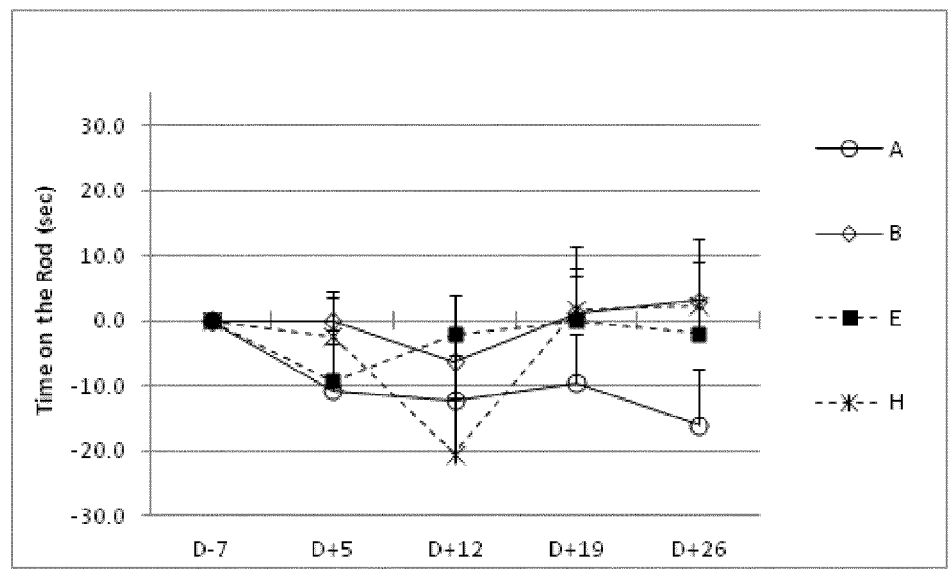

FIG. 19. Kinetics of Time on Rotarod at 23 rpm
X Axis: Days of measured values, according to the protocol.
Y axis: Time gain or loss on Rotarod, relatively to Day −7.
A: Groups A, B, "1 injection" and "2 injections" of Env; B: Groups A, B, C and F;
C: Groups A, B, D and G; D: Groups A, B, E and H.

Figure 20:
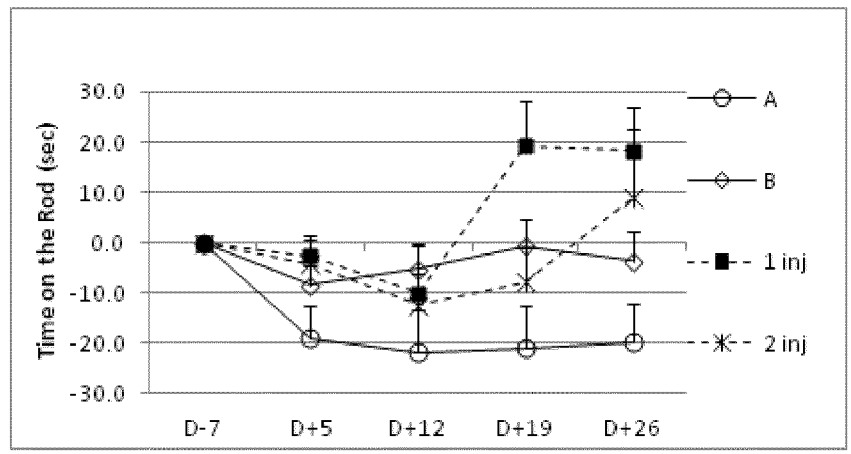
Figure 20:
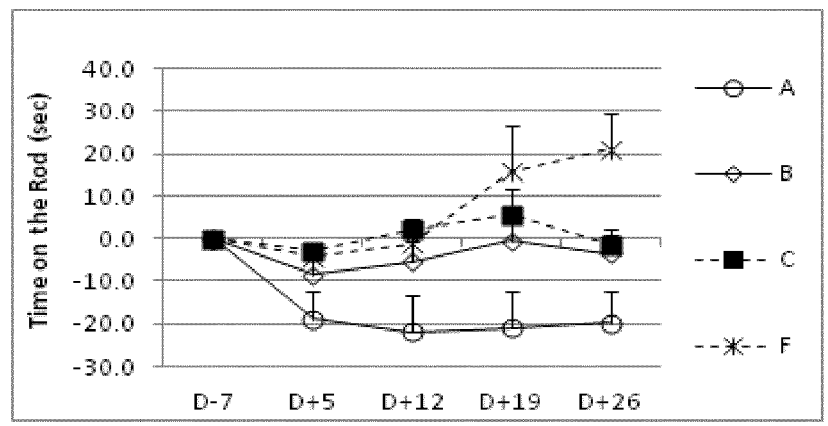
Figure 20:
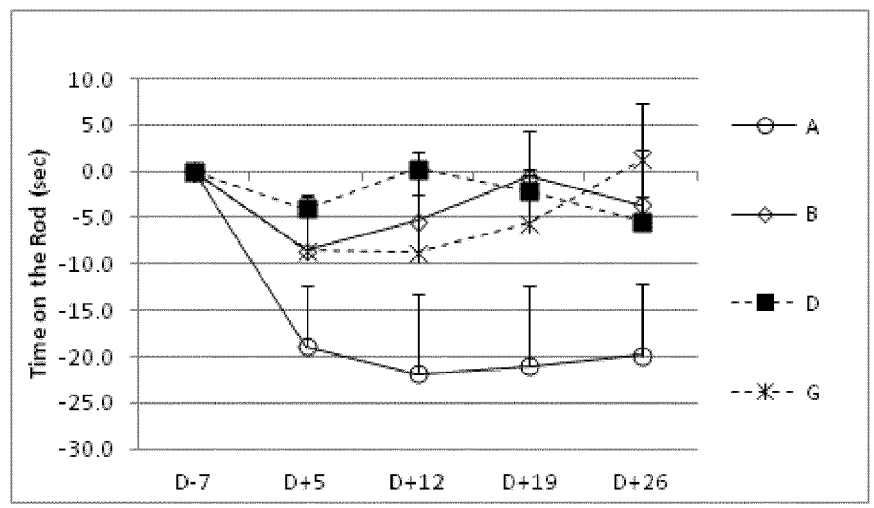
Figure 20:
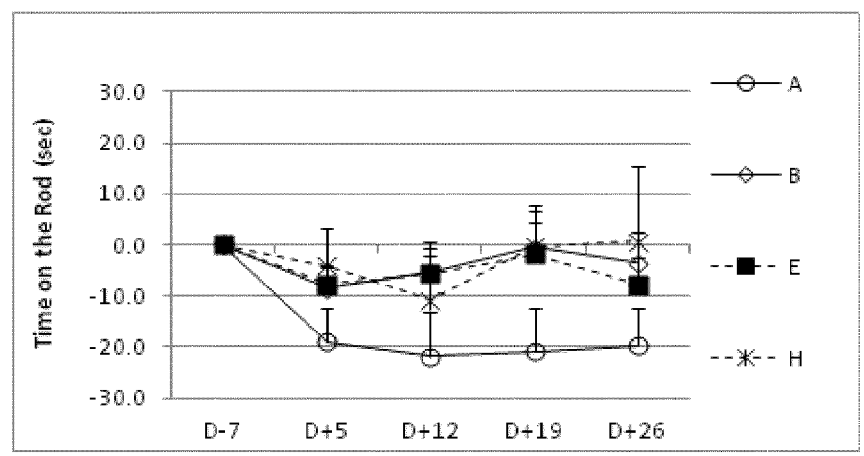

FIG. 20. Kinetics of Time on Rotarod at 26 rpm
X Axis: Days of measured values, according to the protocol.
Y axis: Time gain or loss on Rotarod, relatively to Day −7.
A: Groups A, B, "1 injection" and "2 injections" of Env; B: Groups A, B, C and F;
C: Groups A, B, D and G; D: Groups A, B, E and H.

Figure 21:
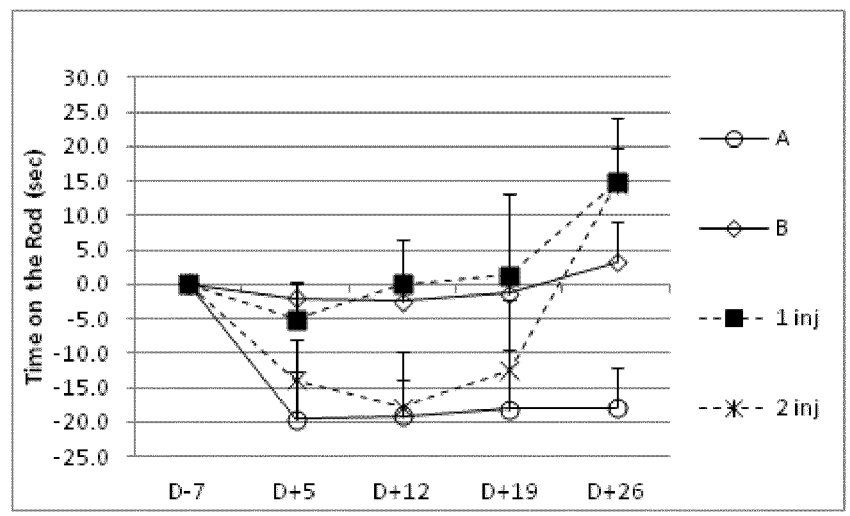
Figure 21:
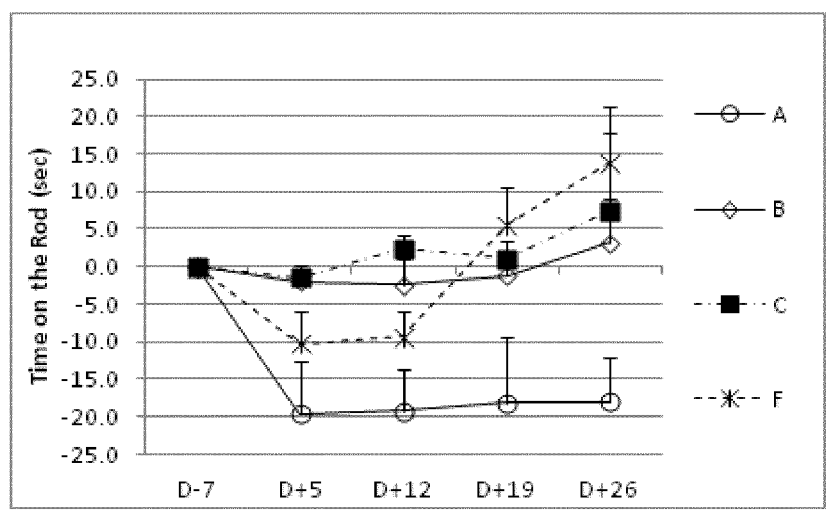
Figure 21:
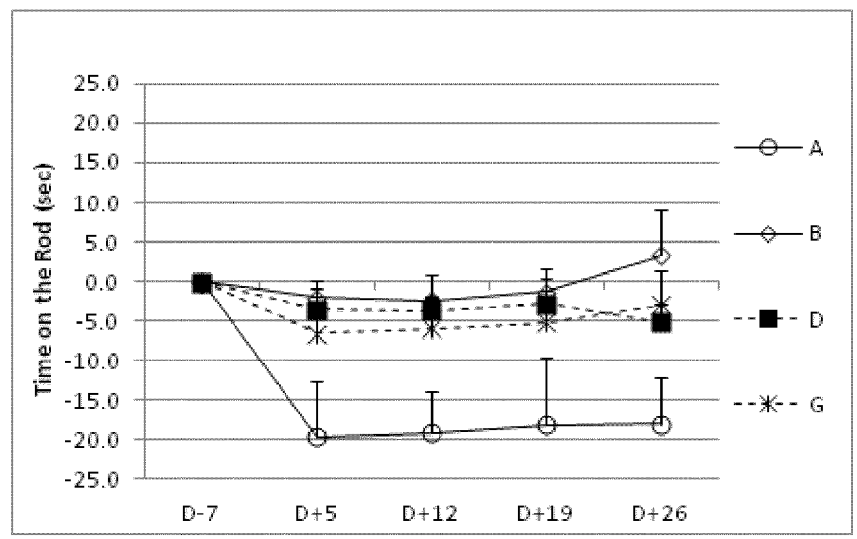
Figure 21:
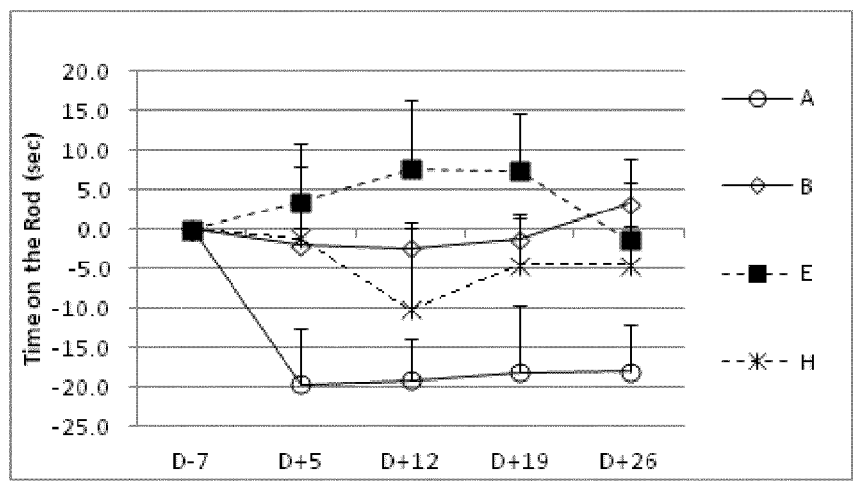

FIG. 21. Kinetics of Time on Rotarod at 29 rpm
X Axis: Days of measured values, according to the protocol.
Y axis: Time gain or loss on Rotarod, relatively to Day −7

A: Groups A, B, "1 injection" and "2 injections" of Env; B: Groups A, B, C and F;
C: Groups A, B, D and G; D: Groups A, B, E and H.

Figure 22:
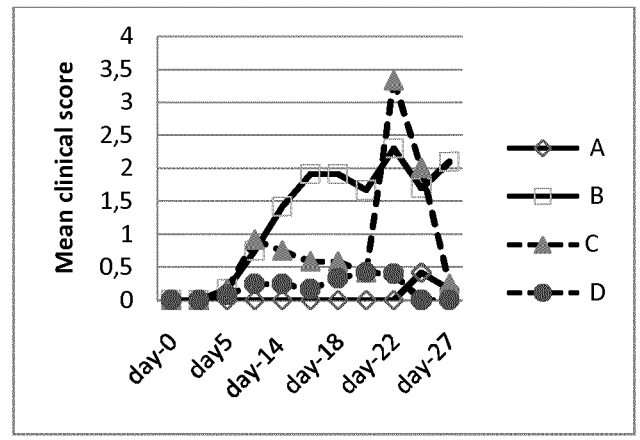

FIG. 22. EAE clinical score kinetics of Groups A, B, C and D (A—Mock EAE negative controls, B—Untreated EAE positive controls, C—EAE treated with GNbAc 200 μg, D—EAE treated with GNbAc 500 μg)

Figure 23:
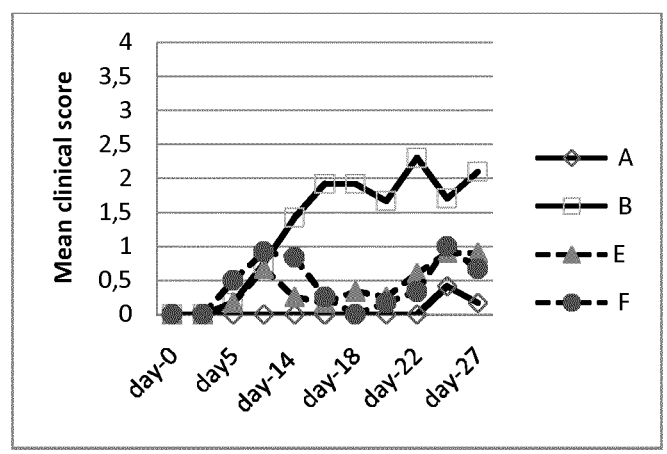

FIG. 23. EAE clinical score kinetics of Groups A, B, E and F (A—Mock EAE negative controls, B—Untreated EAE positive controls, D—EAE treated with SMT, G—EAE treated with GNbAc 200 μg+SMT)

Figure 24:
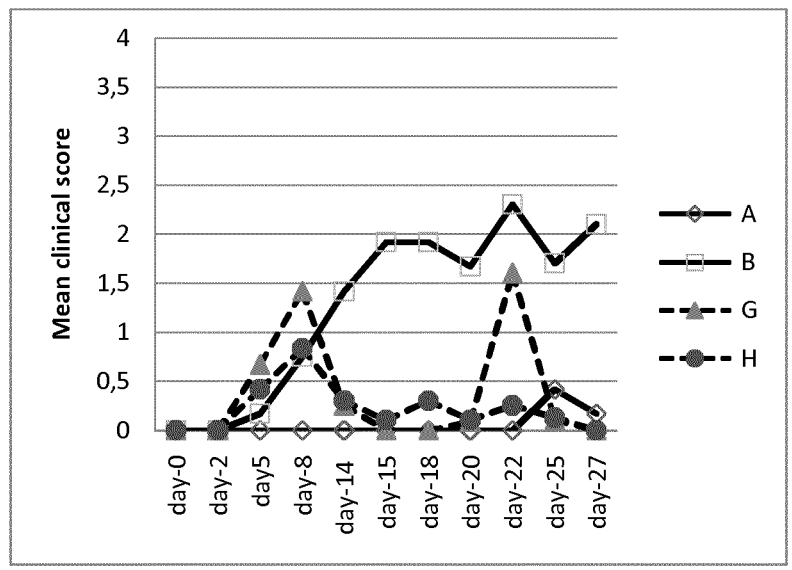

FIG. 24. EAE clinical score kinetics of Groups A, B, G and H (A—Mock EAE negative controls, B—Untreated EAE positive controls, E—EAE treated with DMF, H—EAE treated with GNbAc 200 μg+DMF)

Figure 25:
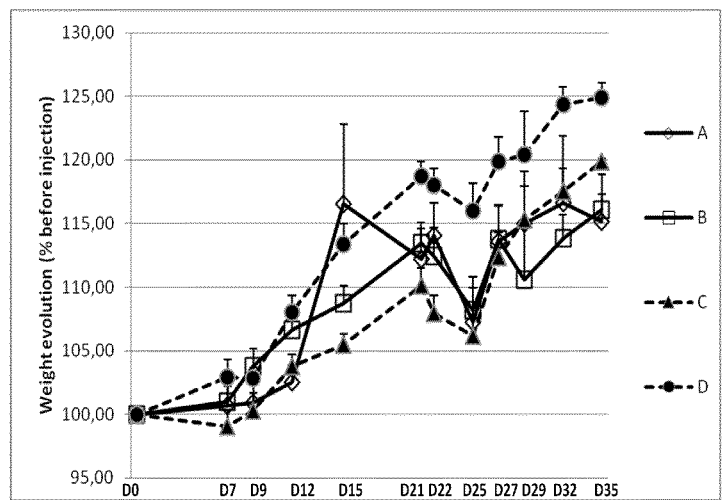

FIG. 25. The weight gain kinetics over the study period (Relative weight gain compared to the day before the first injection of immunogens): Groups A, B, C and D (A—Mock EAE negative controls, B—Untreated EAE positive controls, C—EAE treated with GNbAc 200 μg, D—EAE treated with GNbAc 500 μg)

Figure 26:
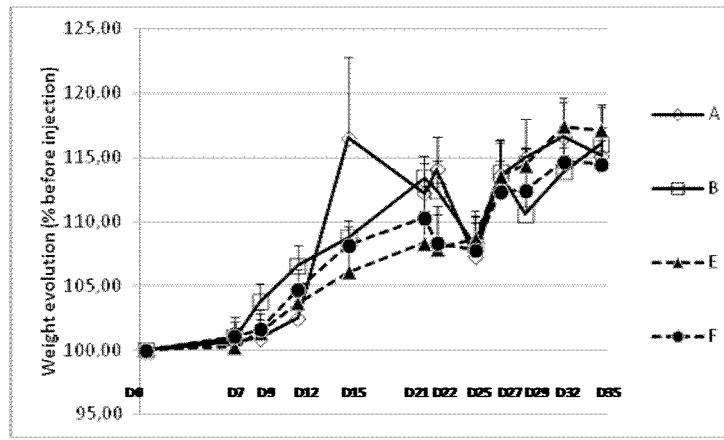

FIG. 26. The weight gain kinetics over the study period (Relative weight gain compared to the day before the first injection of immunogens): Groups A, B, E and F (A—Mock EAE negative controls, B—Untreated EAE positive controls, D—EAE treated with SMT, G—EAE treated with GNbAc 200 μg+SMT)

Figure 27:
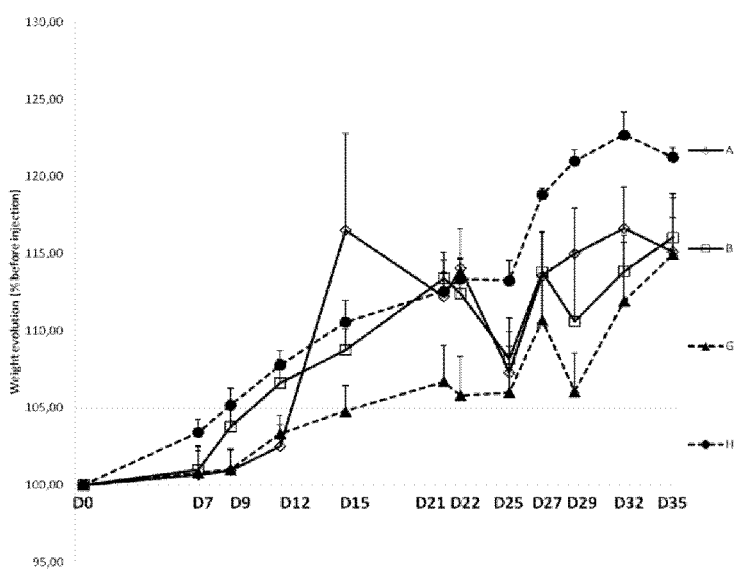

FIG. 27. The weight gain kinetics over the study period (Relative weight gain compared to the day before the first injection of immunogens): A, B, G and H (A—Mock EAE negative controls, B—Untreated EAE positive controls, E—EAE treated with DMF, H—EAE treated with GNbAc 200 μg+DMF)

Figure 28:
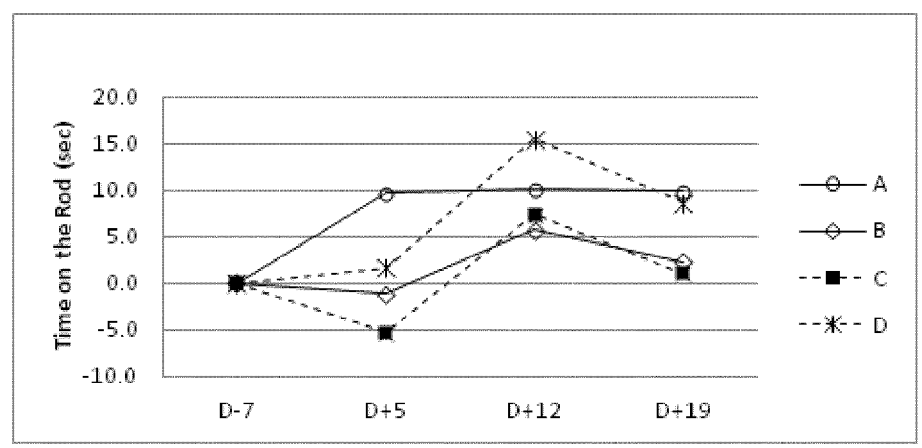
Figure 28:
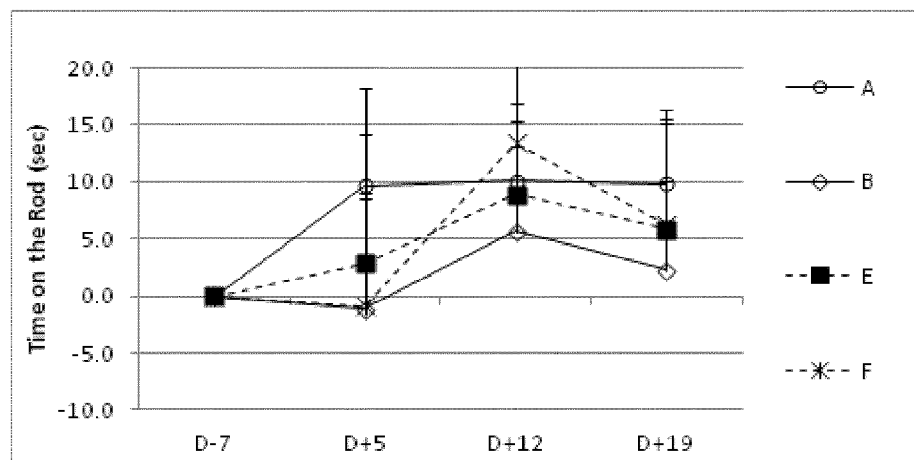
Figure 28:
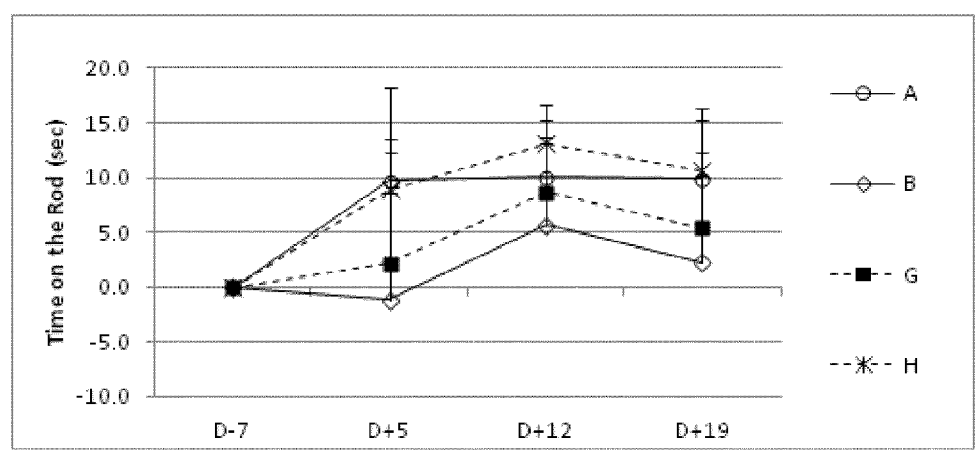

FIG. 28. Kinetics of Time on Rotarod at 16 rpm
X Axis: Days of measured values, according to the protocol.
Y axis: Time gain or loss on Rotarod, relatively to Day −7
A: Groups A, B, C and D; B: Groups A, B, E and F; C: Groups A, B, G and H.

Figure 29:
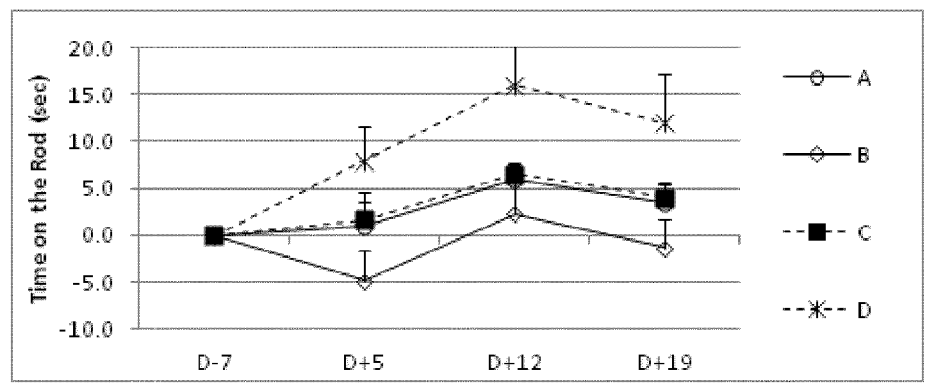
Figure 29:
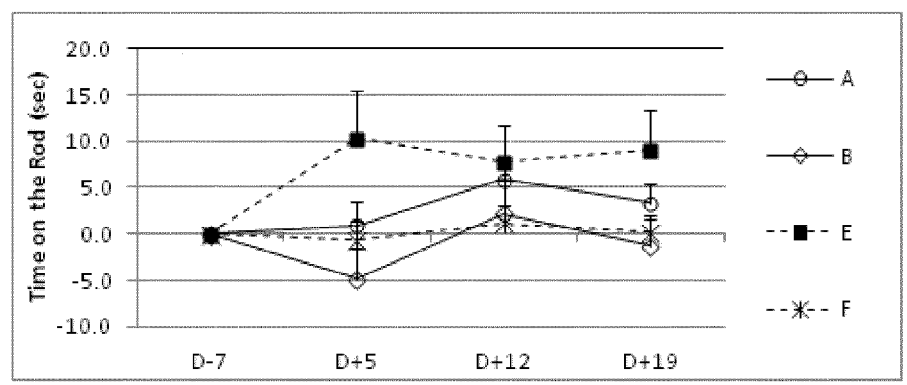
Figure 29:
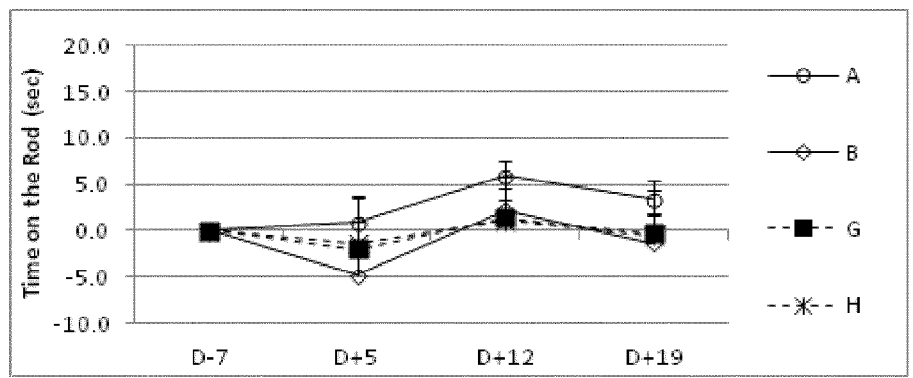

FIG. 29. Kinetics of Time on Rotarod at 26 rpm
X Axis: Days of measured values, according to the protocol.
Y axis: Time gain or loss on Rotarod, relatively to Day −7
A: Groups A, B, C and D; B: Groups A, B, E and F; C: Groups A, B, G and H.

Figure 30:
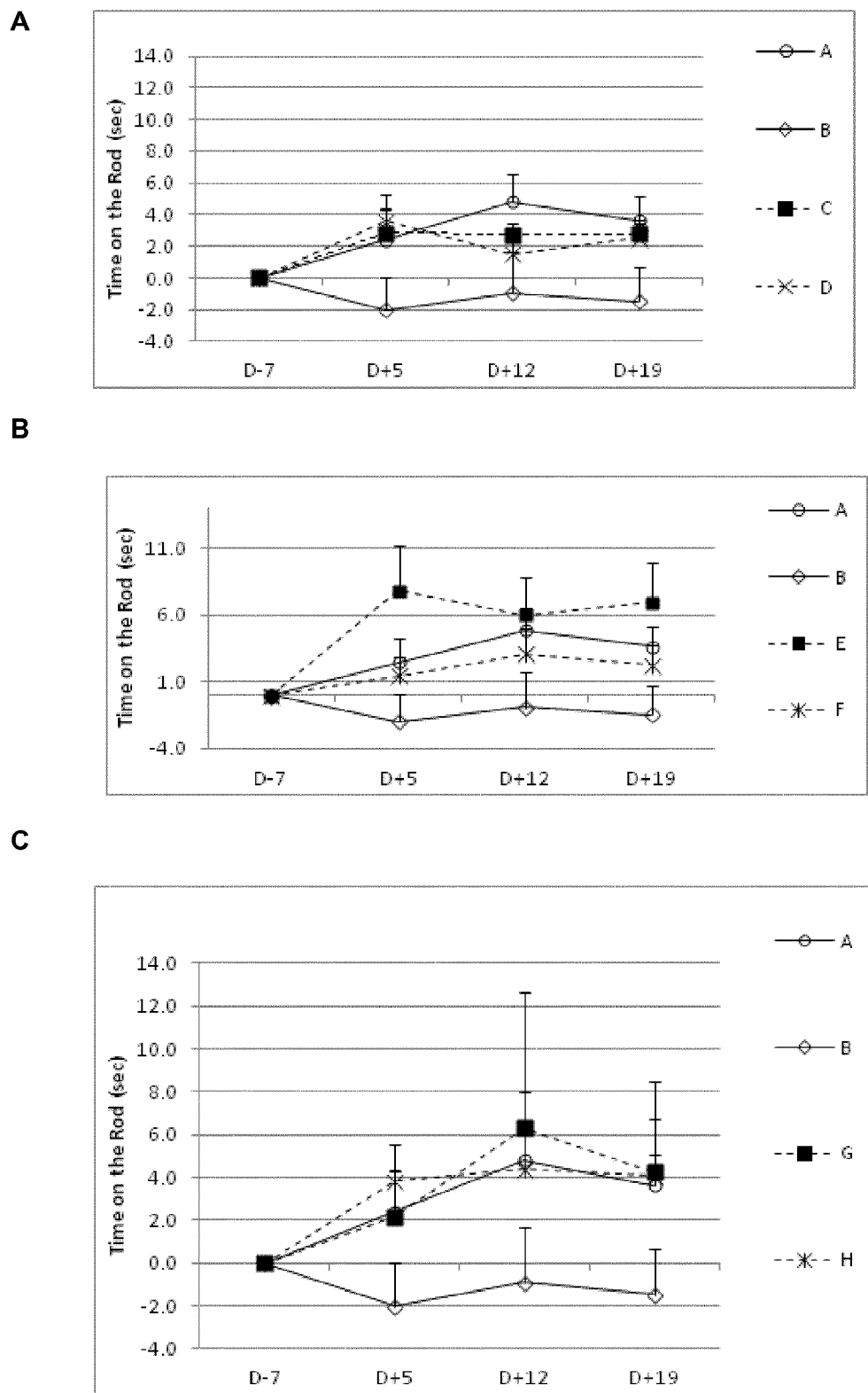

FIG. 30. Kinetics of Time on Rotarod at 29 rpm
X Axis: Days of measured values, according to the protocol.
Y axis: Time gain or loss on Rotarod, relatively to Day −7
A: Groups A, B, C and D; B: Groups A, B, E and F; C: Groups A, B, G and H.

Figure 31:
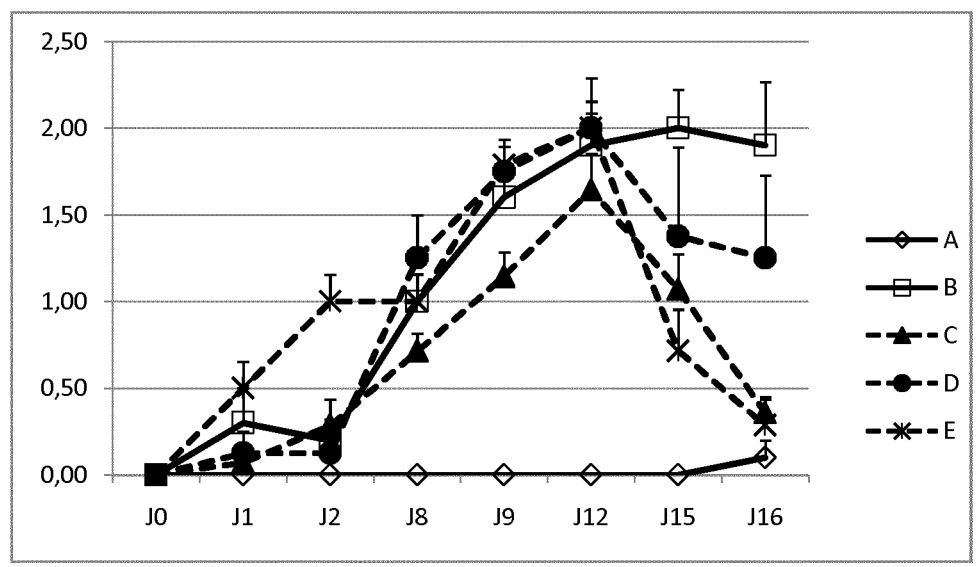

FIG. 31. EAE clinical score kinetics of all groups over the study period (A—Mock EAE negative controls, B—Isotype antibody mock-treated EAE positive controls, C—EAE treated with GNbAc 500 μg, D—EAE treated with Sodium Fumarate and E—EAE treated with GNbAc 500 μg+Sodium Fumarate)

SUMMARY OF THE ABBREVIATIONS USED

| Abbreviation | |
|---|---|
| 3-NT | 3-nitrotyrosine |
| ANOVA | Analysis of variance |
| APC | Adenomatous polyposis coli |
| C57bl/6 | Name of a strain of black mice. |
| CDR | complementary-determining regions |
| CIPD | Chronic Inflammatory Demyelinating Polyneuropathy |

-continued

| Abbreviation | |
|---|---|
| CNPase | cyclic nucleotide 3'-phosphodiesterase |
| DAPI | diamino-2-phenylindol |
| DMF | dimethyl fumarate |
| D-NAME | D-N$^G$-nitroarginine methyl ester |
| EAE | experimental autoimmune encephalomyelitis |
| eGFP | enhanced green fluorescent protein |
| Env | envelope protein |
| FBS | fetal bovine serum |
| FITC | Fluoresceine |
| GalC | galactocerebroside |
| HERV-W | human endogenous retrovirus type W |
| huGAPDH | human glyceraldehyde 3-phosphate dehydrogenase |
| huiNOS | human inducible nitric oxide synthase |
| HuSH | Abbreviation for a certain DNA construct |
| IFA | Incomplete Freund's adjuvant |
| iNOS | Inducible nitric oxide synthase |
| IRAK1/4 | interleukin-1 receptor-associated-kinase-1/4 |
| iv | intravenous |
| LAL | limulus amebocyte lysate |
| LDL | Low density lipid |
| L-NAME | L-N$^G$-nitroarginine methyl ester |
| LSD | Fischer LSD post-hoc analyses = Name of statistical tests |
| MBP | myelin basic protein |
| MC | Methocel |
| MOG | Myelin oligodendrocyte glycoprotein |
| MS | Multiple Sclerosis |
| MSRV | Multiple Sclerosis associated retrovirus |
| NAWM | Normal Appearing White matter |
| NFκB | nuclear factor κ-light-chain-enhancer of activated B cells |
| NO | nitric oxide molecules or nitric oxide radicals. |
| NS | Nervous System |
| O4 | Name of a specific epitope present on oligodendroglial cells |
| ODC | ornithine decarboxylase |
| OPC | Oligodendrocyte precursor cells |
| OPCGS | OPC growth solution |
| OPCM | OPC culture medium |
| PBS | phosphate buffered saline |
| PDGFRα | Alpha-type platelet-derived growth factor receptor |
| PFA | paraformaldehyde |
| pGFP | Green flusorescent protein |
| PTX | pertussis toxin |
| QC | Quality Control |
| riNOS | Rat iNOS |
| RNS | reactive nitrogen species |
| SCID | Severe Combined Immunodeficiency |
| SEM | standard error of the mean |
| shRNA | small-hairpin RNA |
| SMT | S-méthyl- isothiourea |
| SNAP | S-Nitroso-N-acetyl-DL-penicillamine |
| TLR4 | Toll-Like receptor 4 |
| TNFα | Alpha-type Tumor Necrosis Factor |
| TRIF | TIR-domain-containing adapter-inducing interferon-β |
| ΔΔCt | Standardized Unit for relative quantification of RNA |

The following examples are illustrative and are not intended to limit the invention.

Example 1: The Remyelination Blockade Induced by HERV-W Family Envelope Protein (Inhibits Oligodendroglial Precursor Cell Differentiation in Demyelinated Lesions of the Nervous System 1.1 Material and Methods
1.1.1 Oligodendrocyte Precursor Cell Culture Rat oligodendrocyte Precursor Cells (OPCs) were purified as previously described[22]. OPCs were either kept in proliferation medium (Sato medium supplemented with 10 ng/ml recombinant human basic fibroblast growth factor and 10 ng/ml recombinant human platelet-derived growth factor-AA; R&D Systems, Wiesbaden-Nordenstadt, Germany), whereas differentiation was initiated by Sato medium supplemented with 0.5% fetal calf serum. Human fetal oligodendrocyte precursor cells (hOPC) and respective media were purchased from 3H Biomedical, Uppsala, Sweden. Recombinant Env was produced and purified by PX-Therapeutics (Grenoble, France) according to QC specifications of GeNeuro (Geneva, Switzerland) that supplied the protein batches. Endotoxin levels were <5 EU/mL as measured by the limulus amebocyte lysate (LAL) test. Env stimulation was carried out using three different approaches using i) recombinant full length Env protein diluted in differentiation medium at 10 ng/ml, 100 ng/ml and 1000 ng/ml, ii) recombinant Env protein coated on cell culture dishes at a surface concentration of 17.53 ng/cm$^2$ and iii) by seeding OPCs on transfected U343 glioblastoma cells overexpressing Env, respectively. Control stimulation experiments were conducted using the recombinant Env buffer preparation (20 mM histidine, 5% (w/v) sucrose, 0.01% (w/v) polysorbate 20, pH 6.0) at equal dilutions. NO concentration measurements in OPC supernatants were performed using a colorimetric nitric oxide assay kit (Merck-Millipore/Calbiochem, Darmstadt, Germany) and the absorbance was determined at 540 nm using an Anthos plate reader 2001 (Anthos labtec instruments, Salzburg, Austria). OPC morphology assessment was carried out using an anti-O4 antibody Merck-Millipore/Chemicon, Darmstadt, Germany) taking into account cell diameter and the degree of process branching. IRAK-1/4 inhibitor I (1-(2-(4-Morpholinyl)ethyl)-2-(3-nitrobenzoylamino)benzimidazole, N-(2-Morpholinylethyl)-2-(3-nitrobenzoylamido)-benzimidazole; SigmaAldrich, Hamburg, Germany) experiments were performed at a concentration of 2400 nM, TRIF inhibitory peptide (Invivogen, San Diego, USA) experiments were performed at a concentration of 50 μM according to the manufacturer's protocols. Env inactivation was carried out by exposing recombinant Env to a temperature of 123° C. for 1 h. TLR4-antibody receptor blocking experiments were conducted at an antibody concentration of 15 μg/ml. L-NAME/D-NAME blocking experiments were performed at a concentration of 100 μM each; S-Nitroso-N-acetyl-DL-penicillamine (SNAP) was used at a concentration of 100 ng/ml.

1.1.2 Oligodendrocyte Precursor and U343 Glioblastoma Cell Transfection

OPCs were grown for 24 h in proliferation medium and transfection was performed using the NanoJuice reagent (Merck-Millipore, Darmstadt, Germany) employing an shRNA encoding TLR4 suppression vector based on the HuSH 29 pGFP-V-RS vector (OriGene, Rockville, Md., USA) for proof of anti-TLR4 antibody specificity. For expression of membrane-bound Env in U343 glioblastoma cells a citrine expression vector[9] for visualization of transfected cells was combined with an Env-overexpression (pV14 vector with nt 1 to nt 1629 of HERV-W MSRV-type env gene coding sequence—GenBank AF331500.1—supplied by Geneuro SA, Switzerland) in a ratio of 1:5. A corresponding empty vector was used as control. Transfection of U343 glioblastoma cells was accomplished utilizing Lipofectamine (Life Technologies, Darmstadt, Germany).

1.1.3 Multiple Sclerosis Tissue Stainings

For Olig2/Env double stainings formalin-fixed paraffin-embedded human MS tissue was cut and 5 μm sections were deparaffinized in xylene and rehydrated through graded alcohol into distilled water. Endogenous peroxidase activity was quenched by incubating the slides in 0.3% hydrogen peroxide in methanol. Slides were then rinsed with distilled water and transferred to 10 mM Tris, 1 mM EDTA (pH 9) solution to achieve heat-induced antigen retrieval. Hereafter, slides were cooled to room temperature, rinsed in phosphate buffered saline (PBS) and incubated with both anti-Olig2 (1:300; Merck-Millipore) and anti-Env antibody 3B2H4 (1:500, GeNeuro, Geneva, Switzerland) overnight at 4° C. Next, sections were incubated with Alexa 488-labeled donkey-anti-rabbit (1:400; Life Technologies/Molecular Probes, Darmstadt, Germany) to detect Olig2 and Alexa 555-labeled goat-anti-mouse to visualize Env. For TLR4/PGRFRα doublestainings snap-frozen tissue was cut and 5 μm sections were incubated with anti-TLR4 (1:100; Merck-Millipore) and anti-PDGFα antibody (1:50; eBiosciences, San Diego, Calif., USA) overnight at 4° C. TLR4 was detected using Alexa 488-labeled goat-anti-mouse (1:400; Life Technologies/Molecular Probes) and PDGFRα with biotinylated rabbit-anti-rat (1:500; Vector Laboratories, Burlingame, Calif., USA) and Alexa 647-labeled streptavidin (1:400; Life Technologies/Molecular Probes), respectively. For nuclear stainings, sections were incubated with Hoechst stain solution (1:100; Sigma-Aldrich, Hamburg, Germany) for 1 minute and covered with Vectashield (Vector Laboratories). Microscopical analysis was performed with a Leica TCS SP2 AOBS confocal laser-scanning microscope (Leica Microsystems, Heidelberg, Germany).

1.1.4 Stainings of Cultured Cells

Stainings of paraformaldehyde-fixed cultured cells were performed as described previously[22]. Primary antibodies were diluted as follows: anti-TLR4 antibody (1/1000; Merck-Millipore, Darmstadt, Germany), anti-Env antibody 3B2H4 (1/500; GeNeuro, Geneva, Switzerland), anti-2',3'-cyclic nucleotide 3'-phosphodiesterase (CNPase) antibody (1/1000; Covance, Princeton, N.J. USA), monoclonal anti-myelin basic protein (MBP; 1/1000; Convance, Princeton, N.J., USA), polyclonal anti-myelin basic protein antibody (1:1000; Millipore, Schwalbach, Germany), anti-galactrocerebroside (GalC) antibody, anti-O4 antibody (both 1/1000; Merck-Millipore, Darmstadt, Germany); anti-3-NT antibody (1/1000; Abcam, Cambridge, Mass., USA) and anti-NFκB antibody (1/1000; Abcam, Cambridge, Mass., USA). Alexa Fluor 488- and Alexa Fluor 594-conjugated antibodies (both 1:500) were used for signal visualization. Nuclei were stained with 4',6-diamino-2-phenylindol (DAPI; Roche, Basel, Switzerland).

1.1.5 RNA Preparation, cDNA Synthesis, and Quantitative Reverse Transcription Polymerase Chain Reaction RNA purification from cultured cells was performed using the RNeasy procedure (Qiagen, Hilden, Germany). Isolated RNA was reverse transcribed using the high-capacity cDNA Reverse Transcription Kit (Life Technologies/Applied Biosystems). Quantitative determination of gene expression levels was performed on a 7900HT sequence detection system (Life Technologies/Applied Biosystems) using Power SybrGreen universal master mix (Life Technologies/Applied Biosystems). Primer sequences were determined using PrimerExpress 2.0 software (Life Technologies/Applied Biosystems) and tested for the generation of specific amplicons:

| | (SEQ ID No. 7) |
|---|---|
| TLR4_fwd: | CTGGGTTTCTGCTGTGGACA |

| | (SEQ ID No. 8) |
|---|---|
| TLR4_rev: | AGGTTAGAAGCCTCGTGCTCC |

| | (SEQ ID No. 9) |
|---|---|
| riNOS_fwd: | CTCAGCACAGAGGGCTCAAAG |

| | (SEQ ID No. 10) |
|---|---|
| riNOS_rev: | TGCACCCAAACACCAAGGT |

| | (SEQ ID No. 11) |
|---|---|
| huiNOS_fwd: | TGAGGAGCAGGTCGAGGACT |

| | (SEQ ID No. 12) |
|---|---|
| huiNOS_rev: | TGATAGCGCTTCTGGCTCTTG |

| | (SEQ ID No. 13) |
|---|---|
| huGAPDH_fwd: | TGGACCTGACCTGCCGTCTA |

| | (SEQ ID No. 14) |
|---|---|
| huGAPDH_rev: | AGGAGTGGGTGTCGCTGTTG |

| | (SEQ ID No. 15) |
|---|---|
| TNFα_fwd: | AGCCCTGGTATGAGCCCATGTA |

| | (SEQ ID No. 16) |
|---|---|
| TNFα_rev: | CCGGACTCCGTGATGTCTAAG |

| | (SEQ ID No. 17) |
|---|---|
| IL1β_fwd: | GAAACAGCAATGGTCGGGAC |

| | (SEQ ID No. 18) |
|---|---|
| IL1β_rev: | AAGACACGGGTTCCATGGTG |

| | (SEQ ID No. 19) |
|---|---|
| IL6_fwd: | GTTGTGCAATGGCAATTCTGA |

| | (SEQ ID No. 20) |
|---|---|
| IL6_rev: | TCTGACAGTGCATCATCGCTG |

| | (SEQ ID No. 21) |
|---|---|
| GAPDH_fwd: | GAACGGGAAGCTCACTGGC |

| | (SEQ ID No. 22) |
|---|---|
| GAPDH_rev: | GCATGTCAGATCCACAACGG |

| | (SEQ ID No. 23) |
|---|---|
| ODC_fwd: | GGTTCCAGAGGCCAAACATC |

| | (SEQ ID No. 24) |
|---|---|
| ODC_rev: | GTTGCCACATTGACCGTGAC |

GAPDH and ODC were used as reference genes, and relative gene expression levels were determined according to the ΔΔCt method (Life Technologies/Applied Biosystems). Each sample was measured in quadruplicate; data are shown as mean values±standard deviation, and t-test was applied to determine statistical significance.

1.2 Results 1.2.1 Localization of Env Protein Close to Chronic Active MS Lesions and in the Vicinity of Resident OPCs Using immunohistological analyses we studied Env protein localisation in human brain tissue samples. This revealed the presence of quite abundant Env protein in NAWM close to chronic active MS lesions (CAL, FIG. 1B) as well as at the rims of CALs in close vicinity to Olig2-positive OPCs (FIG. 1C). NAWM in further distance to lesions did not show discernible Env immunoreactivity (FIG. 1A). In order to further evidence the potential impact of the Env protein on, resident OPCs and thereby on relevant myelin repair, we furthermore seeked for TLR4 and platelet-derived growth factor receptor alpha (PDGFRα)-double-positive OPCs. We could detect them in healthy brains (FIG. 1D-D''') and in NAWM of MS patients (FIG. 1E-E'''). This clearly demonstrated that in MS brain, TLR4-positive OPCs can be detected in the vicinity of HERV-W Env expressing cells or of the corresponding secreted protein, which makes them susceptible targets of this TLR-4 pathogenic agonist as described[10]. Nonetheless, this constitutes an unexpected finding and opens still unseen perspectives of application because TLR4 was previously unknown to be expressed in such conditions in OPCs and all the more, as further unraveled, because HERV-W envelope protein such as MSRV-Env could therefore not be foreseen to directly interact with OPCs at this precise step of differentiation with final dramatic effects on their myelinating potential.

1.2.2 TLR4 Expression by Cultured Rat and Human OPCs

Figure 2:
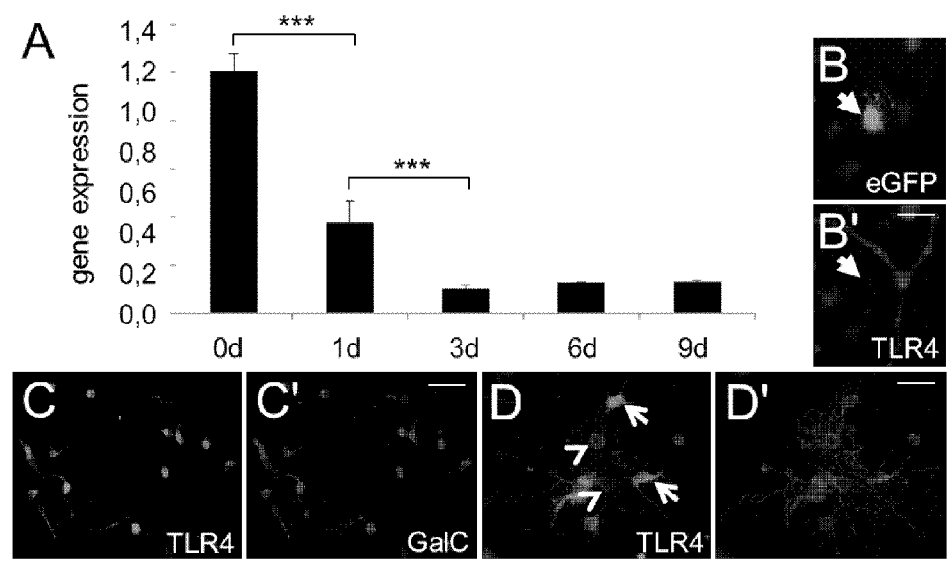

Previous studies had essentially evidenced a TLR4-dependent proinflammatory effect on monocytes and dendritic cells[10]. Anti-TLR4 immunolabeling confirmed the expression of this receptor at the surface of both rat and human oligodendroglial precursor cells (FIGS. 2C,C' and 5B). Moreover, specific shRNA-mediated knockdown of TLR4 in rat OPCs substantiated the specificity of the previous immunolabeling (FIG. 2B,B'). In order to evaluate TLR4 receptor expression kinetics from young to matured OPCs, we performed co-staining using anti-galactocerebroside (GalC) antibody, as well as anti-myelin basic protein (MBP) antibodies, a marker for more mature OPCs, after three and six days of differentiation in culture (FIG. 2C-D'). Interestingly, TLR4 receptor gene expression over time was found to be downregulated during the course of cell differentiation (FIG. 2A), while specific TLR4 protein detection only yielded a weak signal at late time points in morphologically mature rat OPCs s (FIG. 2D) as compared to younger cells.

Figure 3:
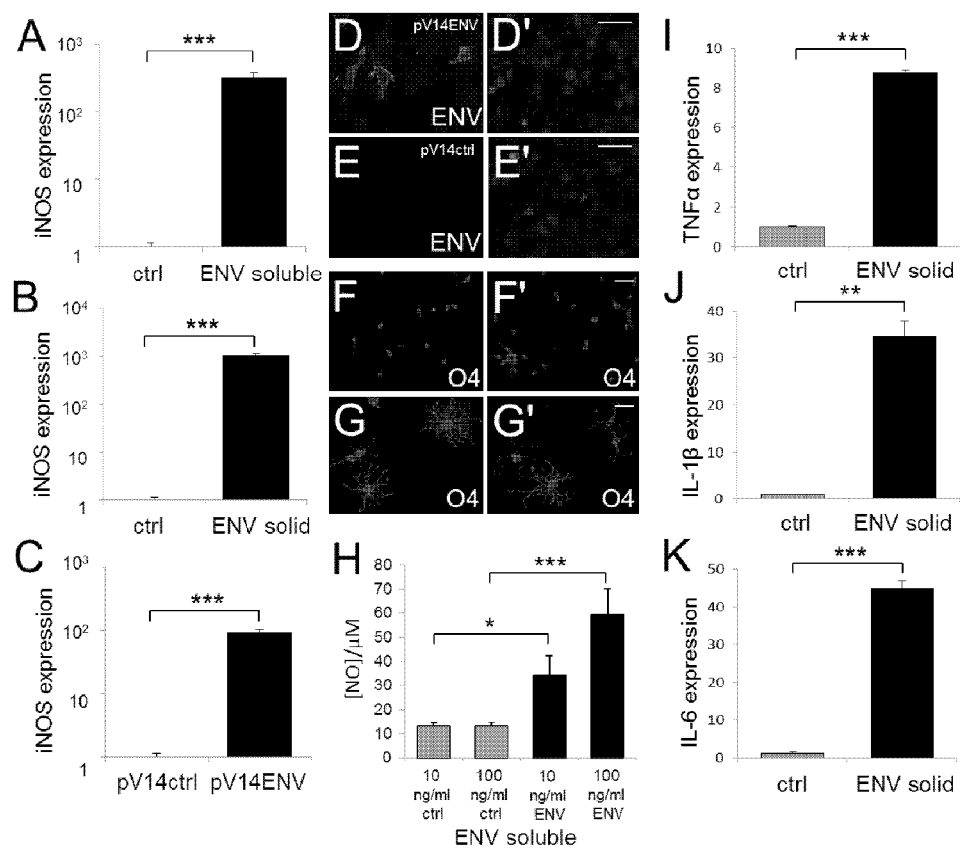
Figure 4:
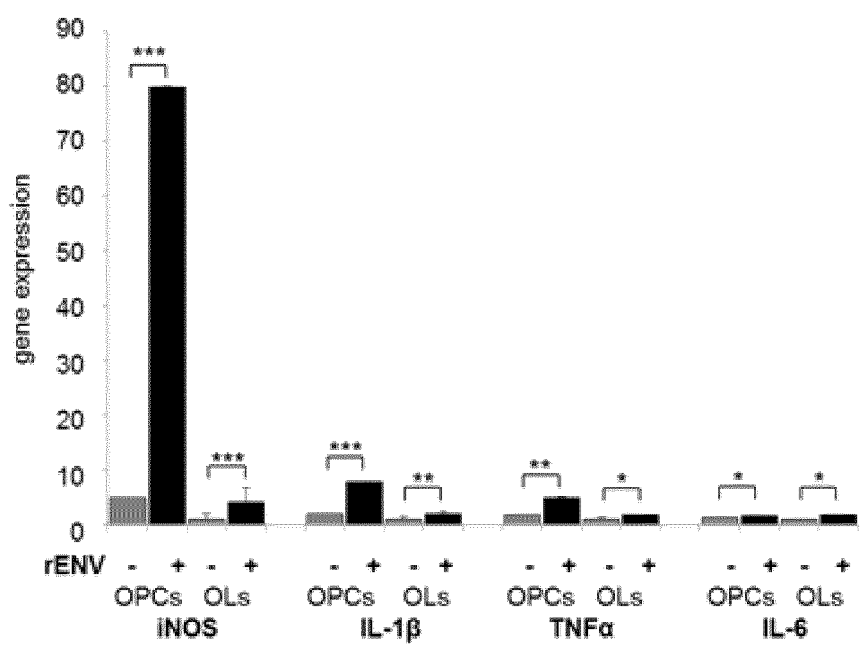
Figure 5:
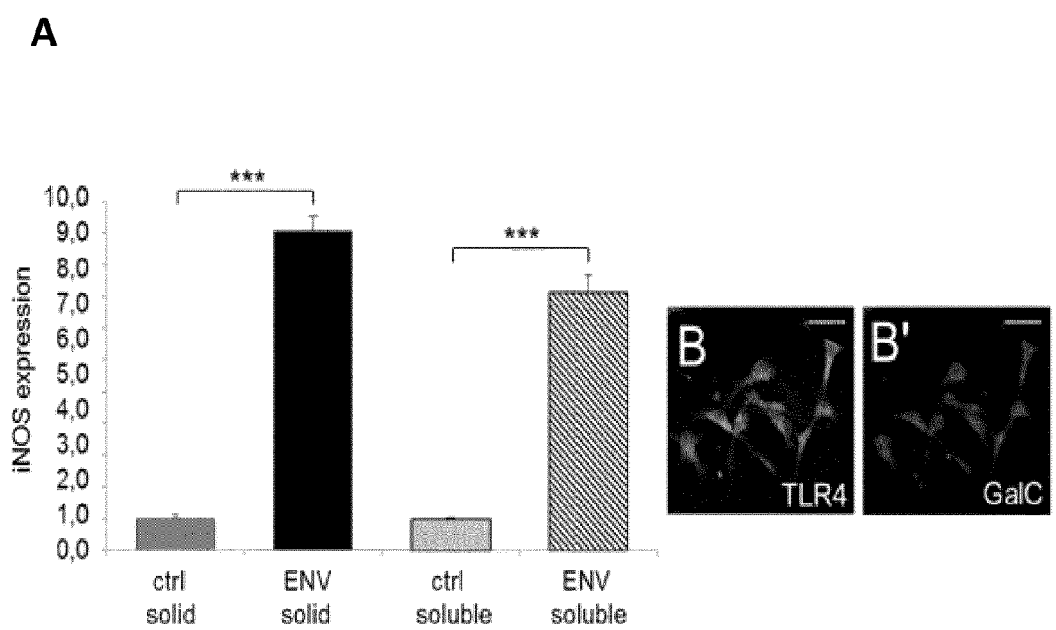

1.2.3 OPC Stimulation by Env Induces Expression of Proinflammatory Cytokines and the Inducible NO Synthase Stimulation of rat OPCs by recombinant Env protein dissolved in medium (Env soluble; 100 ng/ml; FIG. 3A), coated on cell culture dishes (Env solid; FIG. 3B) or overexpressed on the surface of transfected U343 glioblastoma cells (pV14Env; FIG. 3C-E') led to a strong transcriptional increase of the inducible nitric oxide synthase (iNOS) as well as to the induction of proinflammatory cytokines such as TNFα, IL-16 and IL-6 (FIG. 2I-K) as compared to control (buffer or empty vector treated) conditions. In turn, enhanced iNOS expression lead to an Env concentration-dependent rise of its nitrosative stress inducing product nitric oxide (NO) in the cell supernatants (FIG. 3H). Interestingly, rat OPC morphology remained unaltered during Env stimulation as shown by O4 stainings of oligodendroglia performed after one day and five days of Env exposition (FIG. 3F-G'). Human GalC-positive OPCs were also found to express TRL4 (FIG. 5B,B') and stimulation with recombinant Env (both in solution as well as coated on the dish surface) similarly induced iNOS transcription (FIG. 5A). Furthermore, we observed that Env stimulation did not affect OPC survival (as revealed by TUNEL and by quantification of total cell numbers; data not shown) nor induced a senescent OPC phenotype (investigated by (3-galactosidase stainings; data not shown). Env stimulation of matured rat OPCs (matOPCs; kept in differentiation medium for six days) lead to a substantially weaker proinflammatory reaction as determined by transcription levels of iNOS, TNFα, IL-1b and IL-6, in comparison to the effects on immature OPCs (FIG. 4). This observation is in line with the lower TLR4 expression levels found in mature OPCs (FIG. 2) and suggests a superior sensitivity of immature cells towards Env paralleling TLR-4 expression level.

1.2.4 Env Mediates its Effects Via TLR4 and the Proinflammatory Response Involves IRAK-1/4, TRIF and NFκB In order to prove specificity of Env towards TLR4 and to shed further light on downstream signaling we conducted a number of control experiments (FIG. 6). Heat inactivation of recombinant Env prior to OPC stimulation lead to a highly significant decrease of iNOS induction as compared to controls (FIG. 6A). A similar significant reduction of iNOS transcription could be observed using antibody-mediated blockade of TLR4 thereby confirming the specificity of Env towards this receptor and its relevance regarding the observed proinflammatory downstream effects (FIG. 6D). In order to shed light on the intracellular pathways upon TLR4 activation by Env we investigated the roles of the two known downstream pathways following TLR4 activation, the MyD88-dependent pathway involving IRAK-1/4 (interleukin-1 receptor-associated-kinase-1/4) and the MyD88-independent pathway involving TRIF (TIR-domain-containing adapter-inducing interferon-β). Application of IRAK-1/4 inhibitor I or a TRIF inhibitory peptide resulted in significantly decreased iNOS expression levels in presence of Env (FIG. 6B,C) demonstrating that Env-mediated activation of TLR4 leads to the activation of both the MyD88-dependent as well as the MyD88-independent signal transduction pathway. Both pathways can converge on NFκB (nuclear factor κ-light-chain-enhancer of activated B cells) nuclear translocation. Using anti-NFκB antibodies we confirmed that Env stimulation leads to a strong increase of OPCs with nuclear NFκB localisation (FIG. 6E-G') providing an explanation for the observed transcriptional upregulation of proinflammatory cytokines.

1.2.5 Env-Mediated Induction of the Nitrosative Stress Marker Nitrotyrosine

NO, which was significantly increased following Env stimulation (see FIG. 3H), is a reactive nitrogen species (RNS). NO can react with a multitude of intracellular molecules including proteins, nucleic acids and lipids, which results in the formation of 3-nitrotyrosine residues (3-NT). We found that exposition of rat OPCs to recombinant Env protein lead to a strong increase of 3-NT-positive cells in comparison to buffer controls (FIGS. 7B,B' and C,C') indicating NO-mediated nitrosative stress induction. However, upon pre-incubation with the iNOS inhibiting molecule L-NAME (L-N$^G$-nitroarginine methyl ester) NO production was found to be significantly decreased (data not shown), as was the formation of 3-NT positive OPCs (FIG. 7D,D'). When D-NAME, the inactive enantiomer of L-NAME, was used as a negative control, the Env-mediated 3-NT formation was not affected (FIG. 7E,E'). On the other hand, application of SNAP (S-nitroso-N-acetylpenicillamine), a strong NO donor, served as positive control and resulted in nitrotyrosinylation of almost all OPCs (FIG. 7F,F'). Importantly, 3-nitrotyrosine positive OPCs, revealed by their expression of the precursor marker PDGFRα, could also be detected in the NAWM of MS patient brains (FIG. 7G-G''') indicating that this stress mechanism is of pathological relevance in MS.

1.2.6 Env Affects Myelin Expression of OPCs

Following these observations we investigated whether Env protein can affect oligodendroglial differentiation processes shown to be necessary for myelin repair activities. For this purpose, Env stimulated rat OPCs were evaluated for the expression of myelin proteins CNPase (2',3'-cyclic nucleotide 3'-phosphodiesterase) after three days of Env stimulation and MBP (myelin basic protein) after six days of stimulation, respectively. Results revealed that Env strongly reduced the number of CNPase and MBP positive cells (FIG. 8A-D''') as opposed to the unchanged expression of the precursor marker O4 (FIG. 3F-G'). This demonstrated a significantly impaired cellular differentiation reaction in presence of the Env protein. However, the addition of L-NAME but not of D-NAME in parallel to Env stimulation could rescue MBP expression (FIG. 8E-H'), thus evidencing a direct link between 3-NT formation via nitrosative stress and a reduced OPC differentiation capacity.

1.3 Analysis of Results

Inefficient NS remyelination in neuroinflammatory demyelinating diseases such as MS is thought to be primarily caused by a reduced capacity of resident OPCs to differentiate properly and to remyelinate demyelinated axons[11-13], but no major and upstream pathogenic molecule was known to cause this remyelination blockade. Previous studies have already shown that the envelope protein Env of HERV-W, also named "Multiple Sclerosis associated retroviral element" (MSRV) when obtained from corresponding retroviral particles[14], exerts a proinflammatory effect on the innate immune system activating mononuclear cells which, in turn, produce major proinflammatory cytokines[10]. However, a direct link between Env and a reduced OPC differentiation capacity has so far not been, and could not be, envisaged. Here we demonstrate that this Env protein can be detected in MS-affected NS tissue and that Env is capable of interfering with OPC differentiation through a previously unknown presence of Env receptor, TLR4, on OPCs at certain differentiation step(s). This detrimental effect is caused via iNOS. This stress response results in nitrotyrosine formation and directly affects myelin protein expression. Interestingly, Env stimulation did not affect OPC cell survival rates and cellular morphologies remained unaltered suggesting that Env-mediated signals do not target cytoskeletal elements. Of note and confirming the novelty of present unexpected findings, previous studies have claimed an absence of TLR4 on oligodendroglial cells in the human brain[15]. However, in contrast to this former knowledge of the domain, we could clearly demonstrate that TLR4 is not only expressed on cultured primary OPCs (both of rat and human origin) but also on PDGFRα-positive resident human OPCs in MS tissue. Such differences might derive from the fact that Lehnhardt and colleagues used the more general marker O4 for oligodendroglial cell detection while we relied on the newly accepted precursor marker PDGFR-α instead. Nonetheless, we have therefore evidenced this peculiar pattern of TLR4 expression in OPCs for the first time, when this was still believed not to exist. In addition, we observed a strong down regulation of TLR4 during OPC maturation suggesting that receptor expression and, consequently susceptibility to Env, are restricted to immature cells. Nevertheless, this finding is of pathological relevance as it renders these cells capable to interact directly with the Env protein shown to be expressed and released in MS lesions. In the light of these findings we conclude that the MSRV/HERV-W Env protein is not only an immunopathological component of MS but can also exert a significant negative impact on endogenous myelin repair activities. It is therefore concluded that a diminished repair capacity as observed in many MS patients during the disease course is due to the activation of MSRV/HERV-W elements[2]. Of note, a previous study described the experimental effects of an HERV-W Env protein encoded by a defective copy (unable to produce RT-activity nor particles since without coding sequences in gag and pol genes) with stable insertion on chromosome 7[16]. This Env protein can be expressed by the only coding gene of HERV-W 7q element (env, or ERVW-E1 locus), has four aminoacids deletion in the C-terminus part of its surface domain apparently causing a peculiar cellular routing and is known to have in vivo expression at the protein level restricted to placenta[17, 18]. This protein is indeed an example of a "domesticated" HERV protein[17], now playing a physiological role in syncytiotrophoblast tissue formation and therefore named "Syncytin"[19]. The corresponding fusogenic domain in HERV-W Env, as well as the TLR4-binding domain, can be more-or-less conserved between HERV-W sub-types (e.g. MSRV-Env or Syncytin). Their availability as a surface or extracellular protein with conformational exposure of an active domain is highly regulated and the physiological role of Syncytin remains buried in syncytiotrophoblast and limited to the presence of a placenta. Thus an associated pathogenicity appears to be the hallmark of non-physiological activation, e.g., by certain environmental infectious agents[20, 21] in humans, or of experimental transgenic in vitro or in vivo conditions. Syncytin was reported to be found in NS astroglia of individuals with multiple sclerosis (MS), but using an antibody elsewhere reported to detect HERV-W MSRV-Env subtype and not Syncytin[22]. Syncytin sequence could nonetheless be expressed by transgenesis in mouse astrocytes causing the release of cytokines harmful to oligodendrocytes[16], but transgenic mice revealed non-viable (C. Power's personal communication to H. Perron, Neurovirology symposium, San Diego, 2007). However, while Antony and colleagues found adomatosis polyposis coli (APC)-positive myelinating oligodendrocytes to be vulnerable to Syncytin-mediated cytoxicity in such transgenic mouse brains, we were able to demonstrate that only immature OPCs are significantly prone to Env-mediated proinflammatory cues when mature cells are not. Therefore, results from this study are now appearing to results from artefactual experimental conditions linked to their conditions of transgenic forced expression of a placental protein in brain cells. Unlike these results deduced from artificial conditions, we have now revealed a detrimental mechanism which addresses the endogenous repair capacity of the adult nervous system (NS) and not the MS pathology as such, which prominently features an immune-mediated loss of oligodendrocytes and of myelin sheaths with axonal damage. Indeed, Env-mediated effects on immune cells in association with NS inflammatory lesions are now well documented[7, 10, 23-25], but no previous study had evidenced such direct pathogenicity of HERV-W Env on glial cells with an involvement in the blockade of MS plaques remyelination by OPCs. The present results associating MS brain immunohistology showing extensive Env protein expression in active MS plaques or at the rim of less active lesions now support such a role in the known defect in remyelination by OPC in MS lesions.

Example 2: The Remyelination Blockade Induced by HERV-W Family Envelope Protein is Efficiently Treated with Anti-Env Specific Antibody The Envelope protein from HERV-W family envelope (Env, in particular from the Multiple Sclerosis associated RetroVirus subtype, MSRV-Env) is a potent inhibitor of the capacity of non myelinating OPC to differentiate into myelin producing mature oligodendrocytes, which appears as critical step in the remyelination process. We have investigated the effect of MSRV-Env protein on the expression of two different markers of the oligodendrocytes differentiation:

CNPase (2',3'-Cyclic nucleotide-3'-phosphohydrolase) represents 4% of total myelin proteins and is present in the cytoplasm of non-compacted oligodendroglial ensheathment of axons. CNPase is the earliest known myelin-specific protein to be synthesized by developing oligodendrocytes.

MBP (Myelin basic protein) constitutes as much as 30% of myelin proteins and plays a major role in myelin compaction in the central and peripheral nervous systems. It appears sequentially after CNPase both in vivo and in vitro and is a specific marker of mature oligodendrocyte. The aim of the present study was to determine if specific anti-Env antibody such as GNbAC1, a recombinant humanized anti-Env IgG4 monoclonal antibody, can block the inhibition of the OPC maturation induced by MSRV-Env. Indeed, such an effect of GNbAC1 would be indicative of "anti-blockade of remyelinating cells" properties of the antibody. In order to test this hypothesis, human OPC in primary culture were incubated with MSRV-Env, with or without GNbAC1, either by coating the recombinant protein on the culture surface or by adding the protein in the culture medium. The expressions of CNPase (as an early maturation marker) and MBP (as a late maturation marker), were assessed by immunocytochemistry after one or three days of stimulation, respectively.

In the present example, MSRV-Env refers to the full length recombinant MSRV-Env protein which contains intracellular, transmembrane, and extracellular domains of the HERV-W Envelope protein.

The results presented here show that human OPC express specifically TLR4 on their plasma membrane and demonstrate that MSRV-Env recombinant protein specifically and significantly decreases the number of CNPase and MBP positive cells. These observations are in line with those of Example 1 on human and rat OPC. Moreover, our experiments show for the first time that the inhibition (blockade) of human OPC maturation induced by MSRV-Env is completely reversed by a treatment with GNbAC1, demonstrating its novel and previously unexpected therapeutic properties. This consequently provides additional indication in the treatment of progressive forms of multiple sclerosis.

2.1 Material and Methods
2.1.1 Materials
Materials Used for Human OPC Primary Culture

|  | Supplier | Reference | Batch number |
|---|---|---|---|
| Cell incubator | ThermoScientific | HePA Class 100 | — |
| Sterile hood | Fisher Bioblock Scientific | Steril VBH Compact | — |
| Human OPC | 3H Biomedical (ScienCell) | 1600 | 10805 |
| Complete OPC | 3H Biomedical (ScienCell) | 1601 | 10887 |
| Medium |  | 1652 (OPCGS) 0503 (P/S) | 10576 9846 |
| PBS | Gibco | 10010 | 954270 |
| T75 flask | Corning | 2148R | 03412012 |
| Labtek 8-wells | Nunc | 154534 | 081711-8-0 081611-8-0 |
| Poly L-Lysine | Sigma-Aldrich | P4707 | RNBC2451 |
| 10 ml pipettes | Greiner-Bio one | 607180 | 11032401 |
| 5 ml pipettes | Greiner-Bio one | 606180 | 11051101 |

Materials Used for the Assessment of the Maturation Markers Expression in Human OPC

|  | Supplier | Reference | Batch number |
|---|---|---|---|
| PBS | Gibco | 10010 | 954270 |
| Paraformaldehyde | Sigma-Aldrich | 15,812-7 | STBB5309 |
| TritonX100 | Fluka | BP151-100 | 104484 |
| Fetal bovine serum | Sigma-Aldrich | F6178-500ML | 090M8404 |
| Anti-CNPase antibody | Eurogentec (Covance) | SMI91-R | E11BF00277 |
| Anti-MBP antibody | Eurogentec (Covance) | SM99 | E12DF00468 |

-continued

|  | Supplier | Reference | Batch number |
|---|---|---|---|
| Anti-TLR4 antibody | AbNOVA | H00007099-M03 | 11293-1H7 |
| Goat anti-Mouse FITC antibody | Millipore | AP124F | LV1688510 |
| Coverslides | Gerhard Menzel | B7257M | 0290880 |
| Vectashield mounting medium + DAPI | Vector Laboratories | H1500 | X1118 |
| Axioscope microscope | Zeiss | — | — |
| AxioCam | Zeiss | — | — |
| AxioVision software | Zeiss | — | — |

Materials Used for the Stimulation of OPC with MSRV-Env, GNbAC1 and MSRV-Env Buffer

|  | Supplier | Reference | Batch number |
|---|---|---|---|
| Recombinant MSRV-Env | PX'Therapeutics | ENV-T | 110719-1 (22A) |
| MSRV-Env-T Buffer | PX'Therapeutics | — | — |
| GNbAC1 | Polymun | GNbAC1 | T96/bAC1/B1 |

2.1.2 Protocols
Incubation of Human OPC with MSRV-Env, MSRV-Env Buffer and GNbAC1

Full length recombinant MSRV-Env was produced and purified by PX'Therapeutics (548 aa; 61.44 KDa) (batch 110719-1). The initial concentration was 0.6 mg/ml (9.76 µM). MSRV-Env Buffer (20 mM Trizma-HCl, pH 7.5, 150 mM NaCl, 1.5% SDS, 10 mM DTT) was provided by PX'Therapeutics. This solution was used as a negative control. GNbAC1 (Batch T96/bAC1/B1; GMP production) was produced and purified by Polymun Scientific, Vienna, Austria. The initial concentration was 10 mg/ml (68.03 µM).

Human OPC were stimulated with the different treatments either by coating solutions on the cell culture plate surface before cells seeding or by adding them in the cell culture medium after cells seeding. In any case, labtek 8-wells chamber slides (Nunc) were previously coated with poly-L-lysine (Sigma-Aldrich) overnight at 37° C.

Coating of Labtek 8 Wells Chamber Slides

The different treatments were diluted in PBS under a sterile laminar flow hood (Fischer Bioblock, France) and the Labtek 8 wells chambers slides (Nunc; 250 µl per well) were coated as follows:

MSRV-Env (1 µg/ml) coated for 2 hours at 37° C.
MSRV-Env Buffer (same dilution than MSRV-Env) coated for 2 hours at 37° C.
MSRV-Env+GNbAC1 A1: MSRV-Env (1 µg/ml) and GNbAC1 (7.35 µg/ml=50 nM) mixture coated for 2 hours at 37° C.
MSRV-Env+GNbAC1 A2: MSRV-Env (1 µg/ml) and GNbAC1 (29.4 µg/ml=200 nM) mixture coated for 2 hours at 37° C.
MSRV-Env+GNbAC1 B1: MSRV-Env (1 µg/ml) coated for 2 hours at 37° C., washed with PBS and subsequently coated with GNbAC1 (7.35 µg/ml=50 nM) for 1 hour at 37° C.
MSRV-Env+GNbAC1 B2: MSRV-Env (1 µg/ml) coated for 2 hours at 37° C., washed with PBS and subsequently coated with GNbAC1 (29.4 µg/ml=200 nM) for 1 hour at 37° C.
GNbAC1 A1 alone: GNbAC1 (7.35 µg/ml=50 nM) coated for 2 hours at 37° C.

GNbAC1 A2 alone: GNbAC1 (29.4 µg/ml=200 nM) coated for 2 hours at 37° C.

GNbAC1 B1 alone: PBS for 2 hours at 37° C., then coated with GNbAC1 (7.35 µg/ml=50 nM) for 1 hour at 37° C.

GNbAC1 B2 alone: PBS for 2 hours at 37° C., then coated with GNbAC1 (29.4 µg/ml=200 nM) for 1 hour at 37° C.

BSA (1 µg/ml) coated for 2 hours at 37° C.

BSA+GNbAC1 A1: BSA (1 µg/ml) and GNbAC1 (7.35 µg/ml=50 nM) mixture coated for 2 hours at 37° C.

BSA+GNbAC1 A2: BSA (1 µg/ml) and GNbAC1 (29.4 µg/ml=200 nM) mixture coated for 2 hours at 37° C.

BSA+GNbAC1 B1: BSA (1 µg/ml) coated for 2 hours at 37° C., washed with PBS and subsequently coated with GNbAC1 (7.35 µg/ml=50 nM) for 1 hour at 37° C.

BSA+GNbAC1 B2: BSA (1 µg/ml) coated for 2 hours at 37° C., washed with PBS and subsequently coated with GNbAC1 (29.4 µg/ml=200 nM) for 1 hour at 37° C.

Human Oligodendrocyte Precursor Cells Culture

OPC, isolated from human brain tissue, were purchased from ScienCell Research Laboratories (through 3H Biomedical, Sweden). Each vial contains >1×10$^6$ cells in 1 ml. The complete OPC culture medium (OPCM) was reconstituted by addition of OPC growth solution (OPCGS), and penicillin/streptomycin (P/S) to the OPCM according to manufacturer's recommendations (Sciencell).

The vial containing the human OPC was placed in a 37° C. water bath and gently agitated by rotation until the content was completely thawed. The cells were gently resuspended with a 1 ml Gilson pipette. Then, they were diluted in complete OPCM, and seeded into the 8-wells labtek culture vessels (7000 cells/cm$^2$=10000 cells per well) previously coated with poly-L-lysine (0.01%, Sigma) and with (or without) the treatments described above (see 3.2.1.1) under a sterile laminar flow hood (Fischer Bioblock, France). The cultures were incubated at 37° C.; 5% $CO_2$ until subsequent immunocytochemistry experiments. The growth medium was changed the next day to remove the residual DMSO and unattached cells in the cultures treated for 72 hours.

Incubation with MSRV-Env in the Culture Medium

After 3 hours of pre-cultivation (see 3.2.1.2) of the human OPC in the 8-well labtek culture vessels, the cells were incubated at 37° C. for 24 hours or 72 hours in 8-wells labteks (250 µl/well) with the addition of the following solutions:

MSRV-Env Buffer, used as a negative control, added in complete cell culture medium MSRV-Env added at 3 nM (0.184 µg/ml) in complete cell culture medium MSRV-Env (3 nM)+GNbAC1 (200 nM; 29.4 µg/ml) mixture added in complete cell culture medium GNbAC1 (200 nM) alone added in complete cell culture medium Expression of TLR4 and Myelination Markers in OPC In Vitro After 24 or 72 hours of incubation, the cell culture medium was removed and human OPC stimulated by treatments described above (see 3.2.1) were fixed in a paraformaldehyde solution (4% PFA in PBS, 250 µl per chamber) at room temperature for 1 hour. Then, they were washed three times in PBS (3×250 µl per chamber) and non specific binding sites were saturated by incubation with a 10% fetal bovine serum (FBS) in PBS solution containing 0.1% Triton X100 (250 µl per chamber) for 1 hour at 37° C. In the case of TLR4 staining, cells were incubated with 10% FBS in PBS only (250 µl per chamber). After saturation, OPC cultures were incubated with primary antibody solutions overnight at 4° C., diluted in 10% FBS in PBS solution (200 µl per chamber), as follows:

Mouse anti-TLR4 antibodies at 1/1000 (after 24 and 72 hours of culture)

Mouse anti-CNPase antibodies at 1/200 (after 24 hours stimulation)

Mouse anti-MBP antibodies at 1/100 (after 72 hours stimulation)

Cells were washed 3 times in PBS (3×250 µl per chamber), and incubated with secondary antibody solutions for 1 hour at 37° C. (250 µl per chamber), as follows:

FITC conjugated goat anti-mouse antibodies at 1/200

After 3 washes in PBS (3×300 µl per chamber) at room temperature, the plastic chambers were separated from the slides. The slides were then mounted with Vectastain® mounting medium containing DAPI (Vectashield). The stainings were visualized by fluorescent microscopy using an Axioscope microscope (Zeiss).

Data Analyses

After 24 hours of MSRV-Env-T stimulation (or control), CNPase immunoreactive cells were counted in 10 fields per chamber randomly chosen. Percentage of CNPase positive cells was calculated as:

$$\frac{100 \times nCNPase+}{n\ DAPI} n\ CNPase +=$$

number of $OPC$ immunoreactive for $CNPase$

After 72 hours of MSRV-Env-T stimulation (or control), MBP immunoreactive cells were counted in 10 fields per chamber randomly chosen. Percentage of MBP positive cells was calculated as:

$$\frac{100 \times n\ MBP+}{n\ DAPI} n\ MBP += \text{number of } OPC \text{ immunoreactive for } MBP$$

Data were presented as Mean±SEM of percentage of CNPase or MBP positive cells. Graphics were made using GraphPad Software, version 5.00 for Windows (San Diego Calif. USA). Non-parametric statistic tests were performed using Sigma Stat (Chicago, Ill., USA).

The following results were collected during three independent series of experiments, each of them performed with a new vial of frozen commercial OPC: OPC ICC 01, OPC ICC 02, and OPC ICC 03.

2.2 Results 2.2.1 Expression of TLR4 Receptors in Human OPC in Vitro

TLR4 expression was assessed by immunofluorescence microscopy. Saturation step done without any detergent allows the detection of TLR4 on the cell surface only. This experiment confirmed the presence of the target receptor of MSRV-Env at the cell surface of human OPC after 24 and 72 hours of primary culture (not shown).

2.2.2 Expression of CNPase and MBP in Human OPC In Vitro

The morphology of human OPC in vitro was visualized with bright field microscopy. OPC presented a cell body and generally two cellular extensions. CNPase and MBP expressions were confirmed by immunofluorescence microscopy after 24 hours and 72 hours in culture, respectively (not shown).

2.2.3 Effects of MSRV ENV with or without GNbAC1 on Human OPC Differentiation Effect of Coated MSRV-Env on Maturation Markers Expression in Human OPC in Primary Culture (OPC ICC 01)

The aims of this first set of experiments (OPC ICC 01) were to set up human OPC primary culture conditions, as well as labteks chambers slides pre-coating with MSRV-Env and CNPase and MBP immunostaining protocols.

Labtek culture vessels were coated with 1 µg/ml MSRV-Env before seeding the human OPC. As a negative control (buffer), the culture vessels were incubated with the same conditions with MSRV-Env buffer only.

The percentage of CNPase positive cells is significantly decreased from 85±4% in the control condition (buffer) to 69±6% in the human OPC stimulated for 24 hours in labteks pre-coated with MSRV-Env (*p<0.05; t-test) (FIG. 9A).

After 72 hours of culture, the percentage of MBP positive cells is significantly decreased from 74±7% in the control condition (buffer) to 25±3% in labteks pre-coated with MSRV-Env (+Env-T) (*p<0.001 Mann-Whitney Rank Sum test) (FIG. 9B). These results show that MSRV-Env inhibits the maturation of human OPC into myelinating cells in vitro.

Effect of GNbAC1 on the Inhibition of OPC Maturation Induced by MSRV-Env (OPC ICC 02)

The aims of this second set of experiments (OPC ICC 02) were to confirm MSRV-Env effect on human OPC differentiation, and to determine if MSRV-Env can also inhibit human OPC differentiation when the protein is directly added in the cell culture medium. Furthermore, we have also tested if GNbAC1 can inhibit MSRV-Env effects in this model.

In the case of human OPC stimulation in labteks pre-coated with MSRV-Env, GNbAC1 treatments were assessed in two different protocols. First, labtek culture slides were pre-incubated with a mixture of MSRV-Env (1 µg/mL) and GNbAC1 (50 nM or 200 nM) before seeding the OPC (condition GNbAC1-A). The second protocol consisted on a sequential coating with MSRV-Env (1 µg/mL) followed by a coating with GNbAC1 (50 nM or 200 nM) before seeding the OPC (condition GNbAC1-B).

Effects of MSRV-Env and GNbAC1 on CNPase Expression in Human OPC

After 24 hours of stimulation, a significant decrease of the percentage of CNPase positive cells from 75±2% in the control condition (buffer) to 55±2% is observed in labteks pre-coated with 1 µg/ml MSRV-Env (*p<0.001 vs Buffer; One way ANOVA followed by Fischer LSD post-hoc analyses). Moreover, stimulation in labteks pre-coated with 1 µg/ml BSA has no effect on CNPase expression (71±2%), showing that the effect observed with MSRV-Env is specific since it was not seen with a control protein (FIG. 10A).

GNbAC1 significantly inhibits the decrease of CNPase positive cells induced in labteks pre-coated with MSRV-Env (FIG. 10A). The effect of GNbAC1 is seen at 50 nM and 200 nM, and in the two treatments protocols tested: (i) condition GNbAC1-A, 50 nM (69±4%), 200 nM (80±2%); (ii) condition GNbAC1-B 50 nM (96±3%) and 200 nM (76±4%) (ψp<0.001, One-way ANOVA followed by Fisher LSD post-hoc analyses). Furthermore, the effect of GNbAC1 appears to be concentration dependent (FIG. 10A).

Additional control experiments showed that human OPC stimulated for 24 hours in labteks pre-coated with GNbAC1 alone (50 nM or 200 nM), or with a mixture of GNbAC1 (50 nM or 200 nM)+BSA (1 µg/ml) had no effect on the expression of CNPase when compared with the control condition (Buffer) (p>0.05; One-way ANOVA) (FIG. 10B). These observations were made with the two GNbAC1 treatments protocols described previously (GNbAC1-A 50 nM, GNbAC1 A 200 nM and GNbAC1-B 50 nM).

This experiment also demonstrates that even low concentrations of MSRV-Env in solution induce a significant decrease of the percentage of CNPase positive cells after 24 hours, from 78±2% in the control condition (buffer) to 57±2% in the MSRV-Env group (*p<0.001 vs Buffer; One-way ANOVA followed by Fischer LSD post-hoc analyses) (FIG. 11). Furthermore, GNbAC1 (200 nM) treatment fully antagonizes the decrease of CNPase expression induced by MSRV-Env (76±2%; ψp<0.001 vs Env-T; One-way ANOVA followed by Fisher LSD post-hoc analyses). It is interesting to note that 200 nM GNbAC1 alone (74±2%) has no effect on CNPase expression when compared to the control condition (buffer) (FIG. 11).

Effects of MSRV-Env and GNbAC1 on MBP Expression in Human OPC

After 72 hours of stimulation, a significant decrease of the percentage of MBP positive cells from 76±2% in controls (buffer) to 57±1% is observed in labteks pre-coated with 1 µg/ml MSRV-Env (**p<0.001 vs Buffer; One-way ANOVA followed by Fischer LSD post-hoc analyses) (FIG. 12A). In this experiment, OPC culture in labteks pre-coated with BSA (1 µg/ml) show a percentage of MBP positive cells slightly different from the control (buffer) (69±2%). However, BSA effect is also significantly different from the MSRV-Env effect (p<0.001 vs Env-T; One-way ANOVA followed by Fisher LSD post-hoc analysis), and thus reveals to be isolated and non-influencing effect in this experimental series only, since not observed in other experiments or with CNPase in the same series.

GNbAC1 significantly inhibits the decrease of MBP positive cells induced in labteks pre-coated with MSRV-Env (FIG. 12A). A partial effect of GNbAC1 is seen at 50 nM, and a complete inhibition is achieved at 200 nM, and in both treatments protocols tested: (i) GNbAC1-A 50 nM (69±2%) and 200 nM (73±2%) and, (ii) GNbAC1-B 50 nM (68±2%) and 200 nM (74±2%) (ψp<0.001 vs Env-T; One-way ANOVA followed by Fisher LSD post-hoc analyses). Furthermore, the effect of GNbAC1 appears to be concentration dependent (FIG. 12A).

This experiment also demonstrates a significant decrease of the percentage of MBP positive cells from 76±2% in the control condition (buffer) to 55±2% in the cells stimulated by MSRV-Env added in the culture medium (3 nM) for 72 hours (*p<0.001 vs Buffer; One way ANOVA followed by Fischer LSD post-hoc analyses) (FIG. 12B). Moreover, GNbAC1 treatment (GNbAC1 200 nM) completely inhibits the decrease of MBP expression induced by MSRV-Env (76±2%; ψp<0.001 vs Env-T; One-way ANOVA followed by Fisher LSD post-hoc analyses) (FIG. 12B).

Confirmation of GNbAC1 Effects on the Inhibition of OPC Differentiation Induced by MSRV-Env (OPC ICC 03)

Although the results described above were issued from a considerable amount of collected data, the aim of this third set of experiments (OPC ICC 03) was the full replication of GNbAC1 effect in totally independent series of experiments.

Effects of MSRV-Env and GNbAC1 on CNPase and MBP Expressions in Human OPC Cultures After 24 hours of stimulation, a significant decrease of the percentage of CNPase positive cells from 90±1% in the control condition (buffer) to 71±1% is observed in labteks pre-coated with MSRV-Env (1 µg/ml) (*p<0.05; Kruskal-Wallis ANOVA-1 on Ranks followed by Student Newman Keuls post-hoc analysis) (FIG. 13A). As previously described, GNbAC1 (200 nM) completely reverses the inhibition of CNPase expression induced by MSRV-Env in the two GNbAC1 treatments protocols tested (GNbAC1-A: 90±2%, GNbAC1-B: 91±4%) (ψp<0.05 vs Env-T; Kruskal-Wallis ANOVA-1 on Ranks followed by Dunn post-hoc analysis) (FIG. 13A).

After 72 hours of stimulation, a significant decrease of the percentage of MBP positive cells from 78±2% in the control condition (buffer) to 55±3% is observed in labteks pre-coated with MSRV-Env (1 µg/ml) for 72 hours (*p<0.05 vs buffer; Kruskal-Wallis ANOVA-1 on Ranks followed by Dunn post-hoc analysis) (FIG. 13B). As previously described, GNbAC1 (200 nM) completely reverses the inhibition of MBP expression induced by MSRV-Env in the two GNbAC1 treatments protocols tested (GNbAC1-A: 80±2%, GNbAC1-B: 75±2%) (ψp<0.05 vs Env-T; Kruskal-Wallis ANOVA-1 on Ranks followed by Dunn post-hoc analysis) (FIG. 13B).

Pooled Data from Experiments OPC ICC 02 and OPC ICC 03

Results obtained in the two different series of experiments (OPCICCO2 and OPCICCO3) presented above, were pooled in the same analysis. Thus the data plotted of FIG. 14 represent 8 to 14 independent experiments for CNPase (FIG. 14A) and MBP (FIG. 14B). This analysis shows that the MSRV-Env and GNbAC1 effects on human OPC differentiation are highly reproducible and consistent.

In order, to normalize the expression of the data, the control condition (buffer) was used as reference and considered as 100%. In summary, these results show that concentrations of MSRV-Env used in the present series inhibit by 24% the number of CNPase positive cells (CTRL: 100±1%; ENV: 76±1%) and by 27% the number of MBP positive cells (CTRL: 100±2%; ENV: 73±2%). GNbAC1 (200 nM) completely reverses the effect of MSRV-Env on CNPase expression (GNbAC1-A: 102±1%; GNbAC1-B 101±1%) (FIG. 15A), but also the effect on MBP expression (GNbAC1-A: 101±2%; GNbAC1-B 97±2%) (FIG. 15B).

2.3 Analysis of Results

Consequently, data from the present example show that MSRV Env induces a robust and highly reproducible decrease in the expression of two different specific markers of oligodendrocytes maturation. Thus, MSRV Env inhibits the differentiation of human oligodendrocytes precursors into myelinating cells. Furthermore, we clearly demonstrate here that GNbAC1 completely reverses this deleterious MSRV Env effect, and restores the normal levels of CNPase and MBP in this model. These results show that GNbAC1 treats the differentiation blockade of OPC induced by HERV-W/MSRV-Env. Therefore, these results strongly support an innovative indication of GNbAC1 for treating demyelinated lesions induced by HERV-W envelope proteins. This particularly applies to the progressive forms of multiple sclerosis for which remyelination is critical but does not occur from OPC surrounding MS lesions, due to persisting Env-positive cells and secretion as shown in example 1.

Example 3: Study of the Therapeutic Effects of GNbAC1 Antibody, L-NAME, SMT, DMF or Sodium Fumarate in Experimental Allergic Encephalomyelitis (EAE) Murine Model Induced with Myelin Oligodendrocyte Glycoprotein (MOG) and the MSRV/HERV-W Envelope Protein (Env)

3.A Comparison Between Single Molecules (Monotherapy) and Associations of an Anti-Env Antibody with Small Molecules Inhibiting Env-Induced Effectors in OPC Blockade (Combined Therapy).

3.A.1. Material

C57BL/6 mice from Charles River.

MOG 35-55 EspiKem,Srl (Polypeptide company); reference: SC1272.

GNbAc1; batch T950111-8 (Anti MSRV/HERV-W humanized IgG4 antibody comprising each of the complementary-determining regions (CDRs) set forth in SEQ ID No. 1, SEQ ID No. 2, SEQ ID No. 3 SEQ ID No. 4, SEQ ID No. 5 and SEQ ID No. 6.

L-NAME (NGNitro-L-Arg in ine Methyl Ester) Sigma; reference: N5751-5G batch BCBF4375V SMT (S) Mehtylisothiourea hemisulfate (Sigma); reference: M84445-100G batch STBC1003V Dimethyl fumarate (DMF) Sigma; reference: 242926-100G batch 2507VBCBH Methocel MC Sigma; reference: 64605-100G batch BCBD9989V IFA (Sigma) Sigma reference: F5506-10ML batch: 061M8728

PTX (Pertussis Toxin; Calbiochem); Reference: 516561 batch D00128881

PBS (Phosphate buffer saline; Lonza); Reference 516561; batch; D00128881

Env (P'X Therapeutics); Production batches of purified protein validated as endotoxin-free (LDL test<5 UI/ml) and bioactive (Geneuro internal QC tests).

Rotarod apparatus (LE8200; Bioseb France)

3.A.2. Methods

Pathogen free female C57BL/6 mice (6-8 weeks old) were purchased from the Charles River laboratories and maintained at the animal facilities for one week before immunization. One day before immunization, all mice have been weighed, and then evaluated on the Rotarod Test. Rotarod:

Training Days:

9 and 8 days before immunization. Transfer of mice, in their home cages, from the holding room to the experimental room. Mice are habituated to the experimental room for 15 min. During the training period, each mouse was placed on the rotarod at a constant speed (4 rpm) if one mouse was falling, she was back on rotarod, when mice were comfortable on the rotarod, mice were running during 120 sec. All mice were returned to their cage, the speed was increased to 13 rpm and mice were again put on the rotarod for 120 sec. All mice were returned to their cage, the speed was increased to 19 rpm and mice were again put on the rotarod for 120 sec. The experimental-room environment were kept constant between test sessions with respect to temperature, and light intensity.

Test Days:

1 day before each immunization, mice were transferred in their home cages, from the holding room to the experimental room. Mice were habituated to the experimental room for 15 min. Mice then received two trials at 10 increasing speed levels, ranging from 7 to 40 rpm. Individual delays before falling off the rotarod (for the two trials at each speed level) was recorded until 60 sec. Thus, training and performance on the Rotarod system were determined for each animal.

The ROTAROD test results are expressed as kinetics of the mean of individual scores for each group with SEM indicated by bars, for each test day and for each test speed within the discriminating range for neuromotor impairment in present conditions (16 to 29 rpm).

They are calculated for each individual mouse, for each test day and for each speed value, as the relative gain or loss of time on Rotarod (before falling), compared to the first test day at the same speed (D-7, before starting the disease induction in relevant groups). The value is calculated as "Time on Rotarod at dayX"–"Time at Day-7 for the same mouse at the same speed". Figures illustrate the kinetics for the different groups on the whole study period, for representative discriminative speed values when validated to differentiate ill from healthy animals in our conditions (e.g., too high or too low speed values either made healthy ones fall immediately or ill ones capable to sustain a slow movement).

Initial weights and performances data served as our references, in a setting where each animal has been his own control, before mean values and standard deviations per group were calculated. Different groups of animals were housed homogeneously in each cage, according to the corresponding information provided before each experimental series.

sumed around 3.5 ml drinking water per day. Thus, on the basis of this measurement, a dose of 1 mg DMF+0.08% Methocel per mouse were added to 3.5 ml drinking water daily.

350 ng of pertussis toxin (PTX) per animal was injected (i.p.) in all groups on the same day following each immunogen injection, and replicated 2 days later, as usual in EAE protocols in order to facilitate the migration lymphocytes through the blood-brain barrier.

Summarized Presentation of the Experimental Groups of Example 3.A

| Group | MOG (μg) | Env | Diluent | PTX | GNbAc1 | L-NAME | SMT | DMF | n = 48 |
|---|---|---|---|---|---|---|---|---|---|
| A: Untreated EAE | 200 | + | IFA | + | − | — | — | — | 6 |
| B: GNbAc1 | 200 | + | IFA | + | + | — | — | — | 6 |
| C: L-NAME | 200 | + | IFA | + | − | 600 μg/500 μl IP | — | — | 6 |
| D: SMT | 200 | + | IFA | + | − | — | 1 mg in 500 μl IP | — | 6 |
| E: DMF | 200 | + | IFA | + | − | — | — | 1 mg + 0.08% Methocel in 3.5 ml drinking water. Daily. | 6 |
| F: GNbAc1 + L-NAME | 200 | + | IFA | + | + | 600 μg/500 μl IP | — | — | 6 |
| G: GNbAc1 + SMT | 200 | + | IFA | + | + | — | 1 mg in 500 μl IP | — | 6 |
| H: GNbAc1 + DMF | 200 | + | IFA | + | + | — | — | 1 mg + 0.08% Methocel in 3.5 ml drinking water. Daily | 6 |

Clinical Assessment

Animals were weighed and clinically scored 5 days per week according to the following criteria: 0=no signs; 1=tail paralysis or hyper-reflex of hind limb(s) or unilateral hind limb weakness; 2=bilateral hind limb or forelimb weakness; 3=plus unilateral paralysis or major deficit; 4=complete hind limb or forelimb paralysis; 5=plus partial paralysis or major deficit of opposite limbs; 6=moribund or dead. These were adapted from standard criteria, in order to reflect the more rapid induction of brain and cervical cord lesions with this model.

Mice were weighed 3 times a week on Monday, Wednesday and Friday during all experiment.

For the experimental series of Example 3.A, groups were defined as follows.

All groups of 6 (six) mice have been first injected s.c. in the neck on day 0 then in the dorsal flanks on day 7 and 14; with 200 μg of MOG/mouse+60 μg of MSRV-Env+IFA.

Group A was the positive control group of MSRV-Env induced EAE without any treatment.

For Groups G to H, the treatments with GNbAc1, L-NAME, SMT and DMF alone or together with GNbAc1 with the doses indicated below, have been initiated on day 12 post immunization when the progression of EAE clinical symptoms was already observed. GNbAc1 humanized antibody was administered once, but L-Name or SMT was administered every 4 days until termination of the study on day 29. Regarding Groups E and H, attributed for the treatment with DMF, we have previously determined the volume of daily water consumption by each mouse and it has been determined that (in our condition), each mouse con- 3.A.3 Results:

Clinical Observations:

The clinical signs score and weight were evaluated regularly as described above. The EAE score kinetics over the study period is represented in FIGS. 16, 17 and 18.

A regular and persistent evolution of EAE clinical scores such as hyper-reflexia, tail paralysis, hind limb, forelimb weakness and partial paralysis could be recorded in all mice until to the end of the experience in group A (EAE positive control) and until day 12 in other groups which have been treated on day 12 with GNbAc1 humanized antibody (group B) or anti free radicals (group C, D, E) alone or the groups which have been treated simultaneously with GNbAc1 and anti free radicals (groups F, G, H).

Post Treatment Observations:

The clinical signs in the group B treated only 1 time with GNbAc1 diminished slightly up to day 29. In groups treated with only L-NAME, SMT, an irregular recovery could be observed, but with a reduction of EAE progression. It should be mentioned that, on day+16, the injection of SMT was interrupted.

Regarding the groups F, G and H treated simultaneously with GNbAc1 and L-NAME, SMT and DMF respectively, the recovery was much more significant and particularly in groups G and H. These results suggest that synergistic effects significantly accelerate and increase the recovery of EAE symptoms. It is also worth mentioning that treatment with these substances did not cause any abnormality in any group of mice (including control mice tested separately).

According to the results presented in FIGS. 16, 17 and 18, we can summarize that:

the most elevated clinical score (worst disease evolution) is evidenced in untreated animals (group A). Animals treated with GNbAC1 only (group B) improve after its injection (starting from day 12).

groups treated with L-Name or SMT only had lower recovery scores and kinetics than group B.

group E treated with DMF and group F treated with GNbAC1 antibody (200 μg single dose) combined with L-NAME had equivalent recovery at the end of the study.

group G treated with GNbAC1 antibody combined with SMT and group H treated with GNbAC1 antibody combined with DMF had a significantly better recovery at the end of the study and earlier kinetics of clinical improvement than all other groups. This demonstrates the synergistic gain of combining GNbAC1 and SMT, or GNbAC1 and DMF, for a significantly improved therapeutic outcome.

Rotarod Testing

It should first be made explicit that Groups labelled "1 inj" and "2 inj" in FIG. 19 correspond to control animals injected only once (1) or twice (2) with Env protein and MOG antigen, as compared to the three injections of with Env protein and MOG antigen required to induce clinically overt EAE as in all the other groups. They represent control mice exposed to Env below the pathogenic threshold and without clinical disease induction. They confirm that, in order to have all animal tested with various treatments induced to develop an acute and severe EAE symptomatology and evolution, this three injection pattern was required. Therefore, therapeutic effects observed in treated animals are relevant for a treatment efficacy in ongoing and progressing disease conditions.

According the results presented in FIG. 19 with Rotarod scoring at 23 rpm, we can see that:

The physical effort at 23 rpm has reached a sufficient threshold to unravel major sensory and motor dysfunctions in animals: the untreated A group has the worst outcome and kinetics, whereas the animals injected only once or twice ("1inj or 2inj") have significantly milder symptoms and a much better evolution. The pejorative and progressive clinical deficit of untreated group B confirms that disease and corresponding NS lesions were very active with 3 injections of Env. Therefore all other groups with various treatments were subjected to similar potent disease induction by Env.

Group B with EAE treated by a single injection of 200 μg of GNbAC1 has recovered a score similar to control mice without disease induction with low exposure to Env, at the end of the study period.

The most noteworthy effect, under these conditions, is evidenced for group G treated with GNbAC1 antibody combined with SMT that appears to have striking recovery kinetics curve ending with the best score of all groups at the end of the study. This demonstrates the synergistic gain of combining GNbAC1 and SMT for a significantly improved therapeutic outcome.

Group D treated with SMT only also has improved kinetics and outcome (last point of the study period), though to a lesser extent.

According to the results presented in FIG. 20 with Rotarod scoring at 26 rpm, we can see that:

The physical effort at 26 rpm confirms that these conditions are above threshold required within the present experiment for unravelling major sensory and motor dysfunctions in animals: the untreated A group has the worst outcome and kinetics, whereas the animals injected only once or twice ("1inj or 2inj") have significantly milder symptoms and better evolution (very good scores at the end of the study period for the "1inj" group).

Group B with EAE treated by a single injection of 200 μg of GNbAC1 has recovered a score similar to D, G, C, E and H groups and to "2inj" controls, at the end of the study period.

The most noteworthy effect, under these conditions, is evidenced for group F treated with GNbAC1 antibody combined with L-NAME that appears to have good recovery kinetics curve ending with the best score of all groups at the end of the study. Group C treated with L-NAME only also has improved kinetics and outcome, though to a lesser extent. This demonstrates the synergistic gain of combining GNbAC1 and L-NAME for a significantly improved therapeutic outcome.

According to the results presented in FIG. 21 with Rotarod scoring at 29 rpm, we can see that:

The physical effort at 29 rpm still confirms that these conditions are above threshold required for unravelling major sensory and motor dysfunctions in animals: the untreated A group has the worst outcome and kinetics, whereas the animals injected only once or twice ("1inj or 2inj") have significantly milder symptoms and better evolution with similar good scores at the end of the study.

Group B with EAE treated by a single injection of 200 μg of GNbAC1 has recovered a score similar to control mice without disease induction with low exposure to Env, at the end of the study period.

The most noteworthy effect, under these conditions, is evidenced for group F treated with GNbAC1 antibody combined with L-NAME that still appears to have good recovery kinetics curve ending the best score of all groups (end of study). Group C treated with L-NAME only has improved kinetics and outcome, though to a lesser extent.

Another general noteworthy result is the regular improvement of mice from the B group treated with GNbAC1 only, which always displayed greatly stabilized and/or improved scores compared to the untreated animals (group A) in all conditions (16 to 29 rpm tests).

Nonetheless, this obvious efficacy revealed greatly emphasized by the combination of GNbAc1 with L-NAME or SMT. It was also improved by the combination with DMF, but with slower kinetics. Anyhow, this does not preclude better improvement with optimized doses and on longer term treatment.

Thus, in all conditions of testing (including clinical scoring) the combination of SMT, L-NAME or DMF with GNbAC1 provided a significant advantage for clinical and functional recovery, versus the use of any therapeutic molecule given alone. Taken alone the small molecules appear to have lower and quite transient effects, whereas the GNbAC1 has long-lasting effects providing best recovery at the end of the study compared to these small drugs, thus showing prolonged efficacy.

The kinetics and the amplitude of the final recovery being significantly improved with combinations, an advantage of using a combination of the present therapeutic agents for their synergistic and targeted effects on functional recovery is now shown in vivo. This demonstrates an indication for an earlier and more potent clinical efficacy in human disease.

3.B. Comparison of Therapeutic Efficiency of Two Dosages of Anti-Env Antibody Given Alone as Monotherapy, or in Combination with Anti-NO Drugs.

3.B.1 Materials and Methods:
When not specified, all materials and methods were as described for Example 3A.
Experimental Groups
Summarized Presentation of the Experimental Groups of Example 3.B

| Group | MOG 200 µg | ENV 60 µg | DILUENT | PTX 350 ng | GnbAc1 | SMT | DMF |
|---|---|---|---|---|---|---|---|
| A ctrl− | + | / | IFA | + | / | / | / |
| B ctrl+ | + | + | IFA | + | Placebo | / | / |
| C GNbAc1 | + | + | IFA | + | 200 µg | / | / |
| D GNbAc1 | + | + | IFA | + | 500 µg | / | / |
| E SMT | + | + | IFA | + | 200 µg | + | / |
| F SMT | + | + | IFA | + | 500 µg | + | / |
| G DMF | + | + | IFA | + | 200 µg | / | + |
| H DMF | + | + | IFA | + | 500 µg | / | + |

All mice received three injections s.c. on the neck at DO, on the dorsal flank at D7 and D14. Here, mice from Group A were injected with 200 µg/mouse of MOG and IFA only, without Env, thus constituting a negative control group without EAE in the present series (ctrl −). The positive control group with untreated EAE in the present series is represented by Group B (ctrl +). Other groups were injected with 200 µg of MOG/mouse+MSRV-ENV (60 µg)+IFA, with treatments as indicated in the above summarized presentation. Treatments have been initiated on day 12 post immunization in their corresponding groups.

Groups C, E, G received 200 µg of GnbAc1 at J12; Groups D, F, H received 500 µg of GnbAc1 at J12; Group B received only GNbAc1 buffer solution.

Groups E and F received I.P. injection of SMT (200 mg/mouse) twice a week at J12, J14, J19, J21, J26 and J28.

For Groups G and H receiving DMF, we have previously determined the volume of daily water consumption by each mouse and it has been realized that (in our condition), each mouse consumed around 3.5 ml drinking water per day. Thus, on the basis of this measurement, a dose of 2 mg DMF+0.08% Methocel per mouse were added to 3.5 ml drinking water daily.

For each rotarod test speed, results were validated when curves corresponding to untreated mice with Env-induced EAE (Group B, representing positive controls with untreated EAE) showed significant deficit compared to mock-controls (Group A, immunized with MOG diluted in IFA without Env protein). Results were considered as "not interpretable" whenever such criterion was not matched, as corresponding technical and experimental conditions therefore did not pass the quality control based on this significant divergence of curves from "positive versus negative EAE" groups.

After day 20, an intravenous (I.V.) injection with 20 µg of MSRV-Env in physiological saline was made to create an systemic acute challenge by MSRV-Env protein in all mice, when a significant clinical improvement (remission-like) had been obtained with most treatments in EAE mice. This was done on day D21, for mice of groups B, D, F and H, or on day D22, for mice of groups A, C, E and G, This was performed in order to study the response of the different groups to an acute Env antigenemia and to evaluate eventual differences in the protective efficiency of various treatments.

3.B.2 Results:
Clinical Observations
The clinical signs score and weight were evaluated regularly as described above. The EAE clinical score kinetics over the study period are represented in FIGS. 22, 23 and 24. The weight curves, indicating relative weight gain compared to the day before first injection of immunogens, are presented in FIGS. 25, 26 and 27.

Rotarod Testing
Results from Rotarod tests are presented at different speeds (16; 26; 29 rpm) in FIGS. 28, 29 and 30.

This series of experiments addressed the influence of a medium (200 µg) versus high (500 µg) of therapeutic GNbAC1 antibody as a monotherapy and made similar comparisons when combined with SMT and of DMF.

The global comparison of clinical score curves over the study period have been validated since (i) the untreated Env-induced EAE (group B) has the most pejorative evolution and (ii) the mock-immunized controls without EAE (group A) have no detectable clinical signs over the period preceding the intravenous injection (I.V.) of Env on day 20.

Until this iv injection on day 20, all treated groups were significantly and markedly different from the untreated Env-induced EAE. At Day 20, treated groups with different disease kinetics over the study period had comparable score with a mean value below 0.5, indicating a remission period in all treated groups. Which confirmed an efficacy of all antibody dosages and of all tested combinations with either DMF or SMT. Thereafter, the challenge with intraveinous (iv) injection of Env protein on day 20, mimicked a peak of Env expression and its release in the bloodstream, as expected during the initiation of a new and severe relapse of the naturally occurring disease. As shown in FIGS. 22, 23 and 24, it has unraveled significant differences in the therapeutic potency of the different products and doses:

1) GNbAC1 revealed very efficient in conferring resistance to this peak of Env antigenemia at 500 µg dosage (group D), but a transient clinical impairment was seen with 200 µg dosage (group C).
2) In the case of combination with SMT, non significant variations of the clinical score were seen both GNbAC1 dosages (groups E &F). SMT thus conferred an increased resistance to the IV MSRV-Env challenge to mice treated with the lowest GNbAC1 dosage (200 µg) compared to mice treated with the antibody alone at this lower dose (Group C).
3) Mice treated with DMF showed clinical resistance to this peak of antigenaemia when also treated with the higher GNbAC1 dosage (group H) but failed to prevent clinical impairment at the lower dosage (group G). DMF thus did not confer an increased resistance to the IV MSRV-Env challenge to mice treated with the lowest GNbAC1 dosage (200 µg). Mice treated with DMF and higher GNbAC1 dosage (500 µg, in Group H) had comparable resistance than mice treated with GNbAC1 alone at the same dose (Group D).
4) The curves indicating the weight gain over the study period in all groups surprisingly show that group D, treated with GNbAC1 at 500 µg, had the best endpoint.
5) GNbAC1 at 200 µg (group C) or DMF with GNbAC1 at higher dose only (group H), yielded endpoints equivalent to mock-controls.

This indicates that, beyond a relative efficacy of various treatments shown with clinical score kinetics:

GNbAC1 antibody alone at higher dosage (500 µg) displayed the best clinical efficiency. It also had a positive effect on the global health of animals as revealed by the weight gain kinetics.

when combined with GNbAC1 at lower dose (200 µg), SMT revealed to confer significantly increased efficiency to the treatment, with complete resistance to the final MSRV-Env IV challenge.

This indicates that GNbAC1 reveals the most potent treatment, as providing best results with the higher dose (500 µg) but that, at its lower dose (200 μg), it is strongly potentiated by the combination with SMT that efficiently prevented clinical aggravation following the peak of Env antigenemia created by iv injection at the end of the study.

Moreover, these results also suggest that higher dosages of GNbAC1, alone or in combination with present dosage of DMF, would provide a significant gain in therapeutic efficiency on general health (according to weight gain curves).

Nonetheless, an eventual synergy of SMT or DMF with GNbAC1 at higher dose, if existing, cannot be seen since the antibody alone already provides maximal therapeutic efficiency in the present conditions of disease induction and activity in EAE mice.

In parallel, Rotarod analyses objectively confirm, at all relevant speeds (FIGS. 28A, 29A and 30A), that higher dosage of GNbAC1 (500 μg/mouse) is significantly the most efficient product (given alone) in improving the neurological deficit of treated Env-induced EAE mice.

Rotarod testing also confirms the synergistic effects of SMT with GNbAC1, while showing a neurological improvement of animals treated with the lower dose of GNbAC1 combined with SMT showing significant neuromotor improvement at 26 and 29 rpm (FIGS. 29B and 30B). At 16 RPM (FIG. 28B), the lower speed appeared not to provide sufficient discriminating potency for evidencing this clinical gain over the studied period.

Finally, Rotarod results show an improvement in Env-induced EAE mice with DMF at both GNbAC1 dosages, but this becomes clearly significant at 29 rpm only (FIG. 30C).

Consequently, taking into account the results of this objective and automated test assessing the neurological performance of animals, GNbAC1 clearly appears to be a robust treatment when given on a monotherapy basis as presently, in example 3.B. Synergistic effects with anti-NO molecules, as seen with GNbAC1 at lower dose with SMT, are also clearly evidenced and indicate a potent therapeutic gain. This must exist with various dosages of GNbAC1, but could not be seen in the present conditions with already maximal effects of 500 μg of GNbAC1.

3.C. Comparison Between Anti-Env Antibody or Sodium Fumarate Alone (Monotherapy), and Anti-Env Antibody with Sodium Fumarate (Combined Therapy).

3.C.1 Material and Methods

Material

| Item | Supplier | Reference | batch |
|---|---|---|---|
| C57bl/6 | Charles River | / | BEV13587 |
| MOG | polypeptide | SC1272 | TD02019C |
| MSRV-Env | PX'Therapeutics | 24A | 2-20120803 |
| IFA | Sigma | F5506-10ML | 061M8728 |
| PBS | Lonza | BE17-516F | 1MB118 |
| PTX | Calbiochem | 516561 | D00128881 |
| GNbAc1 | (Geneuro) | | T950111-8 |
| Dimethyl fumarate | Sigma | 242926-100G | 2507VBCBH |
| ROTAROD | BIOSEB | LE8200 | / |
| CIMAher isotype ctrl | | | 911028 |

Experimental Groups

| Group | MOG (μg) | ENV | Diluent | PTX | GnbAc1 | Isotype control antibody | Sodium fumarate | n = 28 | Treatment |
|---|---|---|---|---|---|---|---|---|---|
| A) −ctrl | 200 | − | IFA | + | Placebo | — | — | 5 | |
| B) EAE Isotype ctrl | 200 | + | IFA | + | | 500 μg placebo/IP | — | 5 | |
| C) EAE GnbAc1 | 200 | + | IFA | + | 500 μg/IP | — | — | 7 | |
| D) EAE Na2 fum | 200 | + | IFA | + | Placebo | — | 10 mg in 3.5 ml drinking water Daily | 4 | Day + 12 Na2 fum up to the end of experience |
| E) EAE GnbAc1+ Na2 fum | 200 | + | IFA | + | 500 μg/IP | — | 10 mg in 3.5 ml drinking water Daily | 7 | Day + 12 Na2 fum up to the end of experience |

3.C.2 Results:

Clinical Observations:

The clinical signs score and weight were evaluated regularly as described above. The EAE score kinetics over the study period are represented in FIG. 31.

Group A representing negative controls injected with IFA, MOG without Env protein and a placebo injection of antibody consisting in its diluents buffer, never presented significant clinical symptoms during the study period.

An evolution of EAE clinical scores could be recorded until day 12 in groups which have been treated on day 12 with GNbAc1 humanized antibody (group C) or with sodium Fumarate, a DMF-related anti Nitric Oxyde free radicals (anti-NO), alone in group D or simultaneously with GNbAc1 in group E.

Interestingly here, only groups having received high-dose GNbAC1 antibody (C and E) have shown a significant reversion of their clinical score curves and a significantly improved endpoint at the end of the study. Group D treated with Sodium Fumarate only did not reveal any significant clinical improvement compared to Group B treated with an inefficient isotype control antibody (overlapping error bars on the curves). A regular and persistent evolution of EAE clinical scores could be recorded in all mice until to the end of the experience in group B (Env-induced EAE) treated with the isotype control antibody without specificity for the Env protein. This indicates that the therapeutic effects observed with GNbAC1 are specific to this particular antibody and not related to the injection of any humanized antibody with the same isotype that, e.g., would not target the same epitope.

This last example thus shows that:

Control group A without injection of Env protein behaved as healthy controls without clinical signs, despite an injection of all other components required to mock the Env-induce EAE (IFA and MOG) as well as to mock the antibody injection (Diluents of the Antibody); the mock delivery of water soluble sodium Fumarate being implicitly provided by the normal drinking water.

The most elevated clinical score (worst disease evolution) is evidenced in animals treated with the irrelevant isotype control antibody (group B). This mock-isotype antibody injection in presence of Env protein thus revealed to yield a positive EAE control with typical EAE evolution.

Group D treated with Sodium Fumarate only had a bad outcome at the end of the study, similar to Group B treated with an inefficient control antibody.

Groups C and E treated with high dose GNbAC1 antibody alone or combined with Sodium Fumarate had equivalent and significantly good recovery at the end of the study. Clinical improvement appeared from day 15, after treatment had been started.

Here, as Sodium Fumarate alone had no effect and as curve kinetics of groups C and E appear equivalent, the therapeutic effect observed in these two groups must be fully and only caused by GNbAC1 while Sodium Fumarate reveals inefficient.

3.D Analysis of Overall Results from Example 3

In conclusion, alone or combined, treatments with anti-Env specific antibody, such as GNbAc1 and anti-nitric oxide free radicals (anti-NO) compounds, such as DMF, SMT or L-Name, are advantageous because treating and preventing the blockade of the remyelination potential activity induced by HERV-W envelope protein, in particular MSRV-Env, in vitro and in vivo.

GNbAc1 at high dosage (500 µg/mouse of about 20-25 g) also revealed of particular efficiency compared to lower dose (200 µg), when given alone as a monotherapy in the present examples.

REFERENCES

1. Perron H, Garson J A, Bedin F, et al. Molecular identification of a novel retrovirus repeatedly isolated from patients with multiple sclerosis. The Collaborative Research Group on Multiple Sclerosis. *Proc Natl Acad Sci USA*. 1997; 94: 7583-8.
2. Perron H, Germi R, Bernard C, et al. Human endogenous retrovirus type W envelope expression in blood and brain cells provides new insights into multiple sclerosis disease. *Mult Scler*. 2012; 18: 1721-36.
3. Bruno S, Cercignani M and Ron M A. White matter abnormalities in bipolar disorder: a voxel-based diffusion tensor imaging study. *Bipolar Disord*. 2008; 10: 460-8.
4. Goghari V M, Rehm K, Carter C S and MacDonald A W. Sulcal thickness as a vulnerability indicator for schizophrenia. *Br J Psychiatry*. 2007; 191: 229-33.
5. Stevens J R. Neuropathology of schizophrenia. *Arch Gen Psychiatry*. 1982; 39: 1131-9.
6. Perron H, Hamdani N, Faucard R, et al. Molecular characteristics of Human Endogenous Retrovirus type-W in schizophrenia and bipolar disorder. *Transl Psychiatry*. 2012; 2: e201.
7. Perron H, Jouvin-Marche E, Michel M, et al. Multiple sclerosis retrovirus particles and recombinant envelope trigger an abnormal immune response in vitro, by inducing polyclonal Vbeta16 T-lymphocyte activation. *Virology*. 2001; 287: 321-32.
8. Delarasse C, Smith P, Baker D and Amor S. Novel pathogenic epitopes of myelin oligodendrocyte glycoprotein induce experimental autoimmune encephalomyelitis in C57BL/6 mice. *Immunology*. 2013.
9. Heinen A, Kremer D, Gottle P, et al. The cyclin-dependent kinase inhibitor p57kip2 is a negative regulator of Schwann cell differentiation and in vitro myelination. *Proc Natl Acad Sci USA*. 2008; 105: 8748-53.
10. Rolland A, Jouvin-Marche E, Viet C, Faure M, Perron H and Marche P N. The envelope protein of a human endogenous retrovirus-W family activates innate immunity through CD14/TLR4 and promotes Th1-like responses. *J Immunol*. 2006; 176: 7636-44.
11. Chang A, Tourtellotte W W, Rudick R and Trapp B D. Premyelinating oligodendrocytes in chronic lesions of multiple sclerosis. *N Engl J Med*. 2002; 346: 165-73.
12. Kuhlmann T, Miron V, Cui Q, Wegner C, Antel J and Bruck W. Differentiation block of oligodendroglial progenitor cells as a cause for remyelination failure in chronic multiple sclerosis. *Brain*. 2008; 131: 1749-58.
13. Kremer D, Aktas O, Hartung H P and Kury P. The complex world of oligodendroglial differentiation inhibitors. *Ann Neurol*. 2011; 69: 602-18.
14. Komurian-Pradel F, Paranhos-Baccala G, Bedin F, et al. Molecular cloning and characterization of MSRV-related sequences associated with retrovirus-like particles. *Virology*. 1999; 260: 1-9.
15. Lehnardt S, Massillon L, Follett P, et al. Activation of innate immunity in the CNS triggers neurodegeneration through a Toll-like receptor 4-dependent pathway. *Proc Natl Acad Sci USA*. 2003; 100: 8514-9.
16. Antony J M, van Marle G, Opii W, et al. Human endogenous retrovirus glycoprotein-mediated induction of redox reactants causes oligodendrocyte death and demyelination. *Nat Neurosci*. 2004; 7: 1088-95.
17. Bork P, Brown N P, Hegyi H and Schultz J. The protein phosphatase 2C (PP2C) superfamily: detection of bacterial homologues. *Protein Sci*. 1996; 5: 1421-5.
18. Blond J L, Beseme F, Duret L, et al. Molecular characterization and placental expression of HERV-W, a new human endogenous retrovirus family. *J Virol*. 1999; 73: 1175-85.
19. Mi S, Lee X, Li X, et al. Syncytin is a captive retroviral envelope protein involved in human placental morphogenesis. *Nature*. 2000; 403: 785-9.
20. Ruprecht K, Obojes K, Wengel V, et al. Regulation of human endogenous retrovirus W protein expression by herpes simplex virus type 1: implications for multiple sclerosis. *J Neurovirol*. 2006; 12: 65-71.
21. Ruprecht K and Perron H. Exposure to infant siblings during early life and risk of multiple sclerosis. *JAMA*. 2005; 293: 2089; author reply -90.
22. Roebke C, Wahl S, Laufer G, et al. An N-terminally truncated envelope protein encoded by a human endogenous retrovirus W locus on chromosome Xq22.3. *Retrovirology*. 2010; 7: 69.
23. Perron H, Germi R, Bernard C, Garcia-Montojo M, Deluen C and Farinelli L. Human Endogenous Retrovirus type W Envelope expression in blood and brain cells provides new insights into Multiple Sclerosis disease. *Multiple Sclerosis journal.* 2012; DOI: 10.1177/ 1352458512441381.

24. Perron H and Lang A. The human endogenous retrovirus link between genes and environment in multiple sclerosis and in multifactorial diseases associating neuroinflammation. *Clin Rev Allergy Immunol.* 2010; 39: 51-61.

25. Firouzi R, Rolland A, Michel M, et al. Multiple sclerosis-associated retrovirus particles cause T lymphocyte-dependent death with brain hemorrhage in humanized SCID mice model. *J Neurovirol.* 2003; 9: 79-93.

---

The invention claimed is:

1. A pharmaceutical composition comprising:
an anti-HERV-W Env humanized monoclonal IgG4 antibody comprising (i) a light chain variable region including each of the CDRs set forth in SEQ ID No. 1, SEQ ID No. 2, and SEQ ID No. 3, and (ii) a heavy chain variable region including each of the CDRs set forth in SEQ ID No. 4, SEQ ID No. 5, and SEQ ID No. 6; and
a Nitric Oxyde radical (NO) inhibitor selected from the group consisting of S-methyl-isothiourea (SMT) and dimethyl fumarate (DMF).

2. The pharmaceutical composition of claim 1, wherein the NO inhibitor is SMT.

3. The pharmaceutical composition of claim 1, wherein the NO inhibitor is DMF.

4. A pharmaceutical combination product comprising:
a first pharmaceutical composition comprising an anti-HERV-W Env humanized monoclonal IgG4 antibody comprising (i) a light chain variable region including each of the CDRs set forth in SEQ ID No. 1, SEQ ID No. 2, and SEQ ID No. 3, and (ii) a heavy chain variable region including each of the CDRs set forth in SEQ ID No. 4, SEQ ID No. 5, and SEQ ID No. 6; and
a second pharmaceutical composition comprising a Nitric Oxyde radical (NO) inhibitor selected from the group consisting of S-methyl-isothiourea (SMT) and dimethyl fumarate (DMF).

5. The pharmaceutical combination product of claim 4, wherein the NO inhibitor is SMT.

6. The pharmaceutical combination product of claim 4, wherein the NO inhibitor is DMF.

* * * * *

SEQUENCE LISTING

```
<160> NUMBER OF SEQ ID NOS: 30

<210> SEQ ID NO 1
<211> LENGTH: 10
<212> TYPE: PRT
<213> ORGANISM: Mus musculus

<400> SEQUENCE: 1

Ser Ala Ser Ser Ser Val Ser Tyr Met Tyr
1               5                   10

<210> SEQ ID NO 2
<211> LENGTH: 7
<212> TYPE: PRT
<213> ORGANISM: Mus musculus

<400> SEQUENCE: 2

Arg Thr Ser Asn Leu Ala Ser
1               5

<210> SEQ ID NO 3
<211> LENGTH: 9
<212> TYPE: PRT
<213> ORGANISM: Mus musculus

<400> SEQUENCE: 3

Gln Gln Tyr Gln Ser Leu Pro Leu Thr
1               5

<210> SEQ ID NO 4
<211> LENGTH: 5
<212> TYPE: PRT
<213> ORGANISM: Mus musculus

<400> SEQUENCE: 4

Asp Tyr Glu Met His
1               5

<210> SEQ ID NO 5
<211> LENGTH: 17
<212> TYPE: PRT
<213> ORGANISM: Mus musculus

<400> SEQUENCE: 5

Ala Val Ala Pro Glu Thr Gly Gly Thr Ala Tyr Asn Gln Lys Phe Lys
1               5                   10                  15

Gly

<210> SEQ ID NO 6
<211> LENGTH: 7
<212> TYPE: PRT
<213> ORGANISM: Mus musculus

<400> SEQUENCE: 6

Thr Val Val Pro Phe Ala Tyr
1               5
```

```
<210> SEQ ID NO 7
<211> LENGTH: 20
<212> TYPE: DNA
<213> ORGANISM: Artificial Sequence
<220> FEATURE:
<223> OTHER INFORMATION: Primer for amplification

<400> SEQUENCE: 7
ctgggtttct gctgtggaca                                              20

<210> SEQ ID NO 8
<211> LENGTH: 21
<212> TYPE: DNA
<213> ORGANISM: Artificial Sequence
<220> FEATURE:
<223> OTHER INFORMATION: Primer for amplification

<400> SEQUENCE: 8
aggttagaag cctcgtgctc c                                            21

<210> SEQ ID NO 9
<211> LENGTH: 21
<212> TYPE: DNA
<213> ORGANISM: Artificial Sequence
<220> FEATURE:
<223> OTHER INFORMATION: Primer for amplification

<400> SEQUENCE: 9
ctcagcacag agggctcaaa g                                            21

<210> SEQ ID NO 10
<211> LENGTH: 19
<212> TYPE: DNA
<213> ORGANISM: Artificial Sequence
<220> FEATURE:
<223> OTHER INFORMATION: Primer for amplification

<400> SEQUENCE: 10
tgcacccaaa caccaaggt                                               19

<210> SEQ ID NO 11
<211> LENGTH: 20
<212> TYPE: DNA
<213> ORGANISM: Artificial Sequence
<220> FEATURE:
<223> OTHER INFORMATION: Primer for amplification

<400> SEQUENCE: 11
tgaggagcag gtcgaggact                                              20

<210> SEQ ID NO 12
<211> LENGTH: 21
<212> TYPE: DNA
<213> ORGANISM: Artificial Sequence
<220> FEATURE:
<223> OTHER INFORMATION: Primer for amplification

<400> SEQUENCE: 12
tgatagcgct tctggctctt g                                            21

<210> SEQ ID NO 13
<211> LENGTH: 20
<212> TYPE: DNA
<213> ORGANISM: Artificial Sequence
<220> FEATURE:
<223> OTHER INFORMATION: Primer for amplification
```

<400> SEQUENCE: 13
tggacctgac ctgccgtcta                                              20

<210> SEQ ID NO 14
<211> LENGTH: 20
<212> TYPE: DNA
<213> ORGANISM: Artificial Sequence
<220> FEATURE:
<223> OTHER INFORMATION: Primer for amplification

<400> SEQUENCE: 14
aggagtgggt gtcgctgttg                                              20

<210> SEQ ID NO 15
<211> LENGTH: 22
<212> TYPE: DNA
<213> ORGANISM: Artificial Sequence
<220> FEATURE:
<223> OTHER INFORMATION: Primer for amplification

<400> SEQUENCE: 15
agccctggta tgagcccatg ta                                           22

<210> SEQ ID NO 16
<211> LENGTH: 21
<212> TYPE: DNA
<213> ORGANISM: Artificial Sequence
<220> FEATURE:
<223> OTHER INFORMATION: Primer for amplification

<400> SEQUENCE: 16
ccggactccg tgatgtctaa g                                            21

<210> SEQ ID NO 17
<211> LENGTH: 20
<212> TYPE: DNA
<213> ORGANISM: Artificial Sequence
<220> FEATURE:
<223> OTHER INFORMATION: Primer for amplification

<400> SEQUENCE: 17
gaaacagcaa tggtcgggac                                              20

<210> SEQ ID NO 18
<211> LENGTH: 20
<212> TYPE: DNA
<213> ORGANISM: Artificial Sequence
<220> FEATURE:
<223> OTHER INFORMATION: Primer for amplification

<400> SEQUENCE: 18
aagacacggg ttccatggtg                                              20

<210> SEQ ID NO 19
<211> LENGTH: 21
<212> TYPE: DNA
<213> ORGANISM: Artificial Sequence
<220> FEATURE:
<223> OTHER INFORMATION: Primer for amplification

<400> SEQUENCE: 19
gttgtgcaat ggcaattctg a                                            21

<210> SEQ ID NO 20
<211> LENGTH: 21

```
<212> TYPE: DNA
<213> ORGANISM: Artificial Sequence
<220> FEATURE:
<223> OTHER INFORMATION: Primer for amplification

<400> SEQUENCE: 20
tctgacagtg catcatcgct g                                             21

<210> SEQ ID NO 21
<211> LENGTH: 19
<212> TYPE: DNA
<213> ORGANISM: Artificial Sequence
<220> FEATURE:
<223> OTHER INFORMATION: Primer for amplification

<400> SEQUENCE: 21
gaacgggaag ctcactggc                                                19

<210> SEQ ID NO 22
<211> LENGTH: 20
<212> TYPE: DNA
<213> ORGANISM: Artificial Sequence
<220> FEATURE:
<223> OTHER INFORMATION: Primer for amplification

<400> SEQUENCE: 22
gcatgtcaga tccacaacgg                                               20

<210> SEQ ID NO 23
<211> LENGTH: 20
<212> TYPE: DNA
<213> ORGANISM: Artificial Sequence
<220> FEATURE:
<223> OTHER INFORMATION: Primer for amplification

<400> SEQUENCE: 23
ggttccagag gccaaacatc                                               20

<210> SEQ ID NO 24
<211> LENGTH: 20
<212> TYPE: DNA
<213> ORGANISM: Artificial Sequence
<220> FEATURE:
<223> OTHER INFORMATION: Primer for amplification

<400> SEQUENCE: 24
gttgccacat tgaccgtgac                                               20

<210> SEQ ID NO 25
<211> LENGTH: 30
<212> TYPE: DNA
<213> ORGANISM: Artificial Sequence
<220> FEATURE:
<223> OTHER INFORMATION: Coding sequence for CDR
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
```

<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 25
wsngcnwsnw snwsngtnws ntayatgtay 30

<210> SEQ ID NO 26
<211> LENGTH: 21
<212> TYPE: DNA
<213> ORGANISM: Artificial Sequence
<220> FEATURE:
<223> OTHER INFORMATION: Coding sequence for CDR
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 26
mgnacnwsna ayytngcnws n 21

<210> SEQ ID NO 27
<211> LENGTH: 27
<212> TYPE: DNA
<213> ORGANISM: Artificial Sequence
<220> FEATURE:
<223> OTHER INFORMATION: Coding sequence for CDR
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 27
carcartayc arwsnytncc nytnacn                                           27

<210> SEQ ID NO 28
<211> LENGTH: 15
<212> TYPE: DNA
<213> ORGANISM: Artificial Sequence
<220> FEATURE:
<223> OTHER INFORMATION: Coding sequence for CDR

<400> SEQUENCE: 28
gaytaygara tgcay                                                        15

<210> SEQ ID NO 29
<211> LENGTH: 51
<212> TYPE: DNA
<213> ORGANISM: Artificial Sequence
<220> FEATURE:
<223> OTHER INFORMATION: Coding sequence for CDR
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 29
gcngtngcnc cngaracngg nggnacngcn tayaaycara arttyaargg n                 51

<210> SEQ ID NO 30
<211> LENGTH: 21
<212> TYPE: DNA
<213> ORGANISM: Artificial Sequence
<220> FEATURE:
<223> OTHER INFORMATION: Coding sequence for CDR
<220> FEATURE:

```
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 30
acngtngtnc cnttygcnta y                                              21
```